(12) United States Patent
Masuda

(10) Patent No.: US 10,872,998 B2
(45) Date of Patent: Dec. 22, 2020

(54) CHIP SIZE PACKAGE, METHOD OF MANUFACTURING THE SAME, ELECTRONIC DEVICE, AND ENDOSCOPE

(71) Applicant: SONY CORPORATION, Tokyo (JP)

(72) Inventor: Yoshiaki Masuda, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 172 days.

(21) Appl. No.: 16/085,695

(22) PCT Filed: Mar. 10, 2017

(86) PCT No.: PCT/JP2017/009670
§ 371 (c)(1),
(2) Date: Sep. 17, 2018

(87) PCT Pub. No.: WO2017/163927
PCT Pub. Date: Sep. 28, 2017

(65) Prior Publication Data
US 2019/0074399 A1     Mar. 7, 2019

(30) Foreign Application Priority Data

Mar. 24, 2016 (JP) ................................. 2016-060343

(51) Int. Cl.
*H01L 31/12* (2006.01)
*H01L 27/146* (2006.01)
(Continued)

(52) U.S. Cl.
CPC ............ *H01L 31/125* (2013.01); *A61B 1/051* (2013.01); *H01L 25/00* (2013.01); *H01L 25/167* (2013.01);
(Continued)

(58) Field of Classification Search
CPC ...... H01L 31/12; H01L 31/125; H01L 25/167
See application file for complete search history.

(56) References Cited

U.S. PATENT DOCUMENTS 6,337,265 B1 * 1/2002 Trezza .............. H01L 27/14634
257/E31.096
6,485,993 B2 * 11/2002 Trezza ................. H01L 31/167
438/107

(Continued)

FOREIGN PATENT DOCUMENTS

CN     101262002 A     9/2008
CN     103512596 A     1/2014
(Continued)

OTHER PUBLICATIONS

Nakajima, Arata et al., CMOS image sensor integrated with micro-LED and multielectrode arrays for the patterned photostimulation and multichannel recording of neuronal tissue; Opt. Express 20, 6097-6108. (Year: 2012).*

(Continued)

*Primary Examiner* — John P. Dulka
(74) *Attorney, Agent, or Firm* — Chip Law Group

(57) ABSTRACT

The present disclosure relates to a chip size package that enables realization of a compact chip size package in which a solid-state imaging element and a light emitting element are integrated, a method of manufacturing the same, an electronic device, and an endoscope. The chip size package which is an aspect of the present disclosure is provided with a solid-state imaging element which generates a pixel signal according to incident light and a light emitting element which outputs irradiation light according to voltage applied in which the solid-state imaging element and the light emitting element are integrated. The present disclosure is applicable to, for example, a compact electronic device, a medical endoscope, and the like.

14 Claims, 20 Drawing Sheets

(51) Int. Cl.
  *H01L 25/00* (2006.01)
  *H04N 5/225* (2006.01)
  *A61B 1/05* (2006.01)
  *H01L 25/16* (2006.01)
  *H04N 5/369* (2011.01)
  *H01L 33/48* (2010.01)

(52) U.S. Cl.
  CPC .. *H01L 27/14618* (2013.01); *H01L 27/14621* (2013.01); *H01L 27/14623* (2013.01); *H01L 27/14627* (2013.01); *H01L 27/14632* (2013.01); *H01L 27/14636* (2013.01); *H01L 27/14645* (2013.01); *H01L 27/14687* (2013.01); *H04N 5/2253* (2013.01); *H04N 5/2254* (2013.01); *H04N 5/2256* (2013.01); *H04N 5/22521* (2018.08); *H04N 5/369* (2013.01); *H01L 33/486* (2013.01); *H04N 2005/2255* (2013.01)

(56) References Cited

U.S. PATENT DOCUMENTS

| | | | |
|---|---|---|---|
| 7,541,218 B2* | 6/2009 | Hsu | H01L 21/50 257/E21.599 |
| 7,677,943 B2* | 3/2010 | Daniels | F21K 9/90 445/24 |
| 9,538,909 B2* | 1/2017 | Lei | H01L 27/15 |
| 9,570,428 B1* | 2/2017 | Zandian | H01L 33/30 |
| 2007/0165979 A1 | 7/2007 | Oda et al. | |
| 2008/0191333 A1 | 8/2008 | Yang et al. | |
| 2009/0153729 A1* | 6/2009 | Hiltunen | G03B 15/05 348/371 |
| 2010/0096659 A1* | 4/2010 | Noma | H01L 33/486 257/99 |
| 2010/0276572 A1* | 11/2010 | Iwabuchi | H01L 27/14627 250/208.1 |
| 2012/0062113 A1* | 3/2012 | Tang | H01L 33/60 315/32 |
| 2013/0320197 A1* | 12/2013 | Asayama | H04N 5/379 250/208.1 |
| 2013/0320567 A1* | 12/2013 | Thacker | H01L 25/0652 257/777 |
| 2013/0334445 A1 | 12/2013 | Tharumalingam et al. | |
| 2014/0225212 A1 | 8/2014 | Kaschner et al. | |
| 2014/0361200 A1 | 12/2014 | Rudmann et al. | |
| 2015/0087086 A1 | 3/2015 | Yoshida et al. | |
| 2016/0088253 A1 | 3/2016 | Tezuka | |
| 2016/0149076 A1* | 5/2016 | Kitano | H01L 33/26 257/98 |

FOREIGN PATENT DOCUMENTS

| | | |
|---|---|---|
| CN | 104106135 A | 10/2014 |
| CN | 104364898 A | 2/2015 |
| DE | 102008007237 A1 | 8/2008 |
| DE | 102013202170 A1 | 8/2014 |
| EP | 2858106 A1 | 4/2015 |
| JP | 06-153097 A | 5/1994 |
| JP | 11-298803 A | 10/1999 |
| JP | 2004-109516 A | 4/2004 |
| JP | 2005-018595 A | 1/2005 |
| JP | 2007-013002 A | 1/2007 |
| JP | 2007-035779 A | 2/2007 |
| JP | 2008-244437 A | 10/2008 |
| JP | 2013-235867 A | 11/2013 |
| JP | 2014-236183 A | 12/2014 |
| JP | 2015-508509 A | 3/2015 |
| KR | 10-0371251 B1 | 1/2003 |
| KR | 10-2008-0074773 A | 8/2008 |
| KR | 10-2014-0121398 A | 10/2014 |
| TW | 200834938 A | 8/2008 |
| TW | 201401528 A | 1/2014 |
| TW | 201448184 A | 12/2014 |
| WO | 2005/067062 A1 | 7/2005 |
| WO | 2012/029735 A1 | 3/2012 |
| WO | 2013/091829 A1 | 6/2013 |
| WO | 2013/179767 A1 | 12/2013 |
| WO | 2014/196216 A1 | 12/2014 |

OTHER PUBLICATIONS

Tagawa, Ayato et al., Multimodal Complementary Metal-Oxide-Semiconductor Sensor Device for Imaging of Fluorescence and Electrical Potential in Deep Brain of Mouse, Jpn. J. Appl. Phys. 49, 01AG02-1 to 01AG02-5. (Year: 2010).*

T. Tokuda et al., "A CMOS-based on-chip neural interface device equipped with integrated LED array for optogenetics," Annual International Conference of the IEEE Engineering in Medicine and Biology Society, San Diego, CA, 2012, pp. 5146-5149, doi: 10.1109/EMBC.2012.6347152. (Year: 2012).*

International Search Report and Written Opinion of PCT Application No. PCT/JP2017/009670, dated May 9, 2017, 11 pages of ISRWO.

* cited by examiner

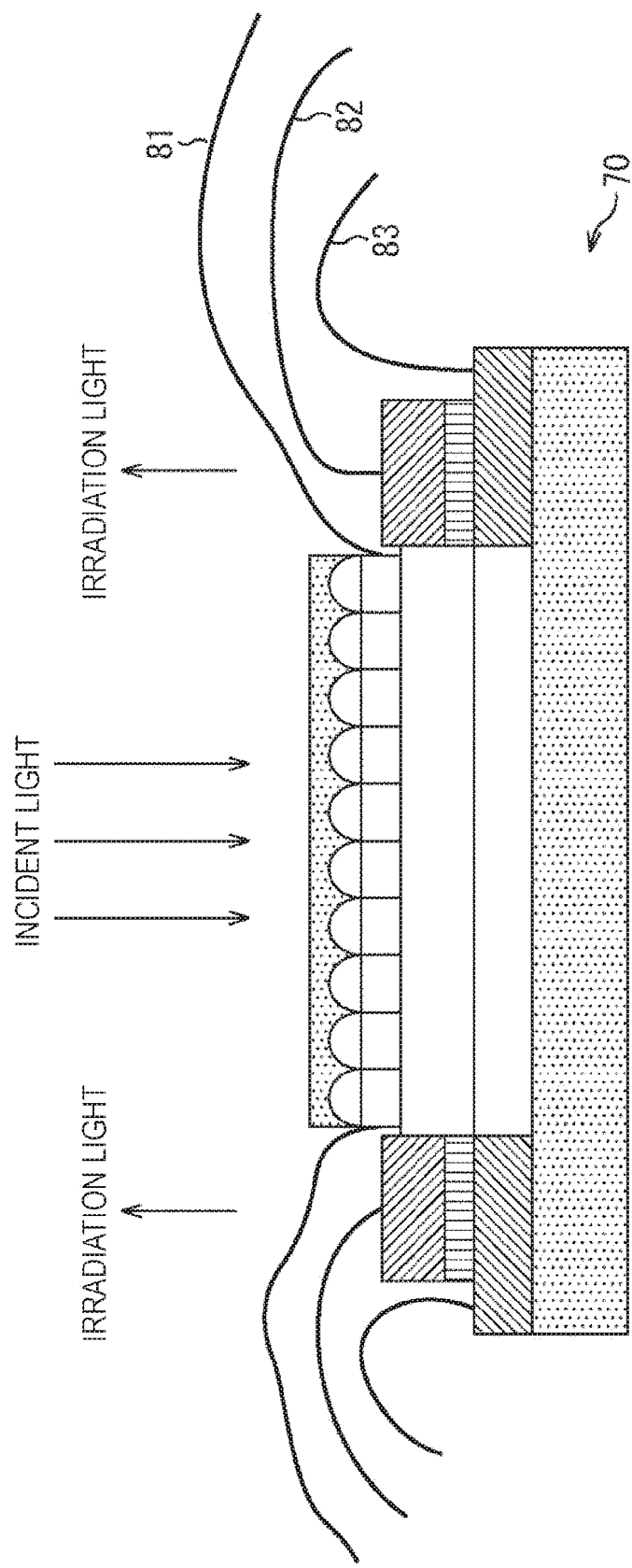

CHIP SIZE PACKAGE, METHOD OF MANUFACTURING THE SAME, ELECTRONIC DEVICE, AND ENDOSCOPE

CROSS REFERENCE TO RELATED APPLICATIONS

This application is a U.S. National Phase of International Patent Application No. PCT/JP2017/009670 filed on Mar. 10, 2017, which claims priority benefit of Japanese Patent Application No. JP 2016-060343 filed in the Japan Patent Office on Mar. 24, 2016. Each of the above-referenced applications is hereby incorporated herein by reference in its entirety.

TECHNICAL FIELD

The present disclosure relates to a chip size package, a method of manufacturing the same, an electronic device, and an endoscope, and especially relates to a chip size package suitable for use in a case of arranging a solid-state imaging element such as a CMOS and a light emitting element such as an LED so as to be adjacent to each other, a method of manufacturing the same, an electronic device, and an endoscope.

BACKGROUND ART

In a camera mounted on a compact electronic device, it is required that a solid-state imaging element represented by CMOS and the like for taking an image and a light emitting element represented by an LED for irradiating a subject with light be arranged adjacent to each other. In order to satisfy this requirement, it is desired to integrate a solid-state imaging element and a light emitting element, and various combination methods are proposed (for example, refer to Patent Document 1).

CITATION LIST

Patent Document

Patent Document 1: Japanese Patent Application Laid-Open No. 2004-109516

SUMMARY OF THE INVENTION

Problems to be Solved by the Invention

In a case of integrating the solid-state imaging element and the light emitting element, in the conventional wafer process, a module of the solid-state imaging element and a module of the light emitting element are combined, so that it is difficult to downsize an entire integrated module. Furthermore, in the wafer process, a process of making the module of the solid-state imaging element, a process of making the module of the light emitting device, and a process of combining both are required, so that the process is complicated.

The present disclosure is achieved in view of such a situation, and an object thereof is to realize a compact chip size package in which the solid-state imaging element and the light emitting element are integrated.

Solutions to Problems

A chip size package according to a first aspect of the present disclosure is provided with a solid-state imaging element which generates a pixel signal according to incident light and a light emitting element which outputs irradiation light according to voltage applied in which the solid-state imaging element and the light emitting element are integrated.

The solid-state imaging element may be obtained by stacking a first layer in which a pixel array that performs photoelectric conversion is formed, and a second layer in which at least a signal processing circuit for processing the pixel signal converted by the pixel array and an I/O circuit are formed, and the signal processing circuit and the I/O circuit formed in the second layer may be arranged so as not to protrude in a lateral direction from a region occupied by the pixel array.

The light emitting element may be formed using sapphire glass as a support substrate.

The sapphire glass may also serve as a cover glass of the solid-state imaging element.

The chip size package according to the first aspect of the present disclosure may be such that a first substrate on which a plurality of light emitting elements is formed and a second substrate on which a plurality of solid-state imaging elements is formed are bonded to each other by a WCSP manufacturing method and then singulated.

The chip size package according to the first aspect of the present disclosure may be such that a plurality of solid-state imaging elements is mounted on a substrate on which a plurality of light emitting elements is formed by a COW manufacturing method and then singulated.

The solid-state imaging element mounted on the substrate on which the plurality of light emitting elements is formed by the COW manufacturing method may be made a CSP, and a solder ball may be formed as a connection terminal on the CSP solid-state imaging element.

A wire may be connected as a connection terminal to the solid-state imaging element mounted on the substrate on which the plurality of light emitting elements is formed by the COW manufacturing method.

The chip size package according to the first aspect of the present disclosure may be such that a plurality of light emitting elements is mounted on a substrate on which a plurality of solid-state imaging elements is formed by a COW manufacturing method and then singulated.

The light emitting element may be an LED element or a laser element.

A moth-eye processed portion for adjusting directivity of the irradiation light output from the light emitting element may be formed on the sapphire glass.

A light shielding wall may be formed at a boundary between the light emitting element and the solid-state imaging element.

A light shielding groove may be formed in the sapphire glass located at a boundary between the light emitting element and the solid-state imaging element.

A method of manufacturing according to a second aspect of the present disclosure is a method of manufacturing a chip size package provided with a solid-state imaging element that generates a pixel signal according to incident light, and a light emitting element that outputs irradiation light according to voltage applied, the solid-state imaging element and the light emitting element being integrated, the method provided with: applying sealing resin to a second substrate on which a plurality of solid-state imaging elements is formed; bonding a first substrate on which a plurality of light emitting elements is formed to the second substrate to which the sealing resin is applied by a WCSP manufacturing method; and singulating the bonded first and second substrates.

An electronic device according to a third aspect of the present disclosure is provided with a chip size package obtained by integrating a solid-state imaging element which generates a pixel signal according to incident light and a light emitting element which outputs irradiation light according to voltage applied.

An endoscope according to a fourth aspect of the present disclosure is provided with a chip size package obtained by integrating a solid-state imaging element that generates a pixel signal according to incident light, and a light emitting element that outputs irradiation light according to voltage applied.

Effects of the Invention

According to the first to fourth aspects of the present disclosure, a compact chip size package (hereinafter, also abbreviated as CSP) may be realized.

BRIEF DESCRIPTION OF DRAWINGS

FIG. 7 is a cross-sectional view illustrating a configuration example of a CSP being a third embodiment.

MODE FOR CARRYING OUT THE INVENTION

Hereinafter, a best mode for carrying out the present disclosure (hereinafter referred to as an embodiment) is described in detail with reference to the drawings.

<Configuration Example of Solid-State Imaging Element Before Integration>

Figure 1:
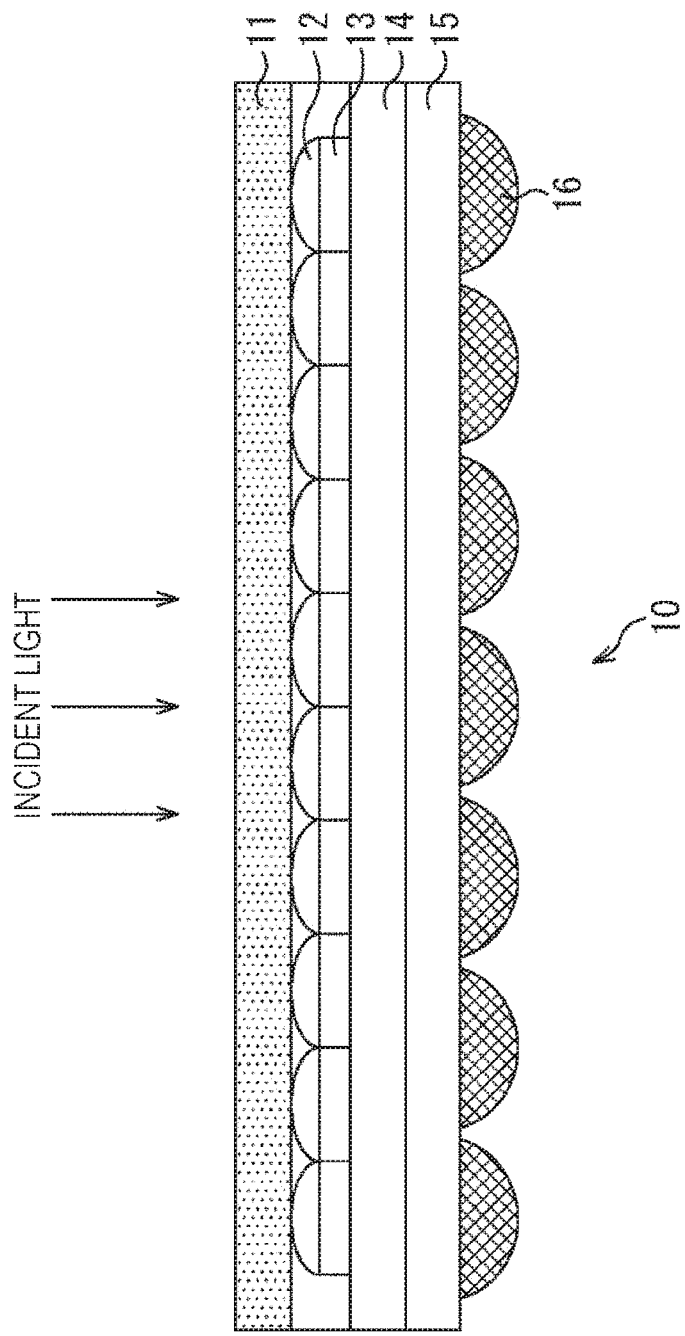
FIG. 1 is a cross-sectional view illustrating a general configuration example of a solid-state imaging element.

FIG. 1 is a cross-sectional view illustrating a general configuration example of a solid-state imaging element before integration.

A solid-state imaging element 10 includes a cover glass 11, an on-chip lens 12, a color filter 13, a photodiode (PD) layer 14, a wiring layer 15, and a solder ball 16 in this order from a light incidence side.

In general, the cover glass 11 includes SiO glass as a material and is polished from a thickness of 500 to 800 μm to approximately 300 μm in a manufacturing process. However, there is a case where the cover glass 11 is omitted at the time of integration with a blue LED element.

The on-chip lens 12 condenses incident light on the PD layer 14. As the color filter 13, respective color filters of R, G, and B, for example, are arranged according to the Bayer array. In the PD layer 14, a PD which is a photoelectric conversion element is formed.

In the wiring layer 15, a predetermined signal processing circuit, an I/O circuit for taking out an external terminal and the like are formed. The signal processing circuit, the I/O circuit and the like formed in the wiring layer 15 are arranged so as not to protrude in a lateral direction from a region occupied by a pixel array formed in the PD layer 14 on an upper layer side.

The solder ball 16 is provided as the external terminal when the solid-state imaging element 10 is mounted on an electronic device and the like.

<Configuration Example of Light Emitting Element Before Integration>

Figure 2:
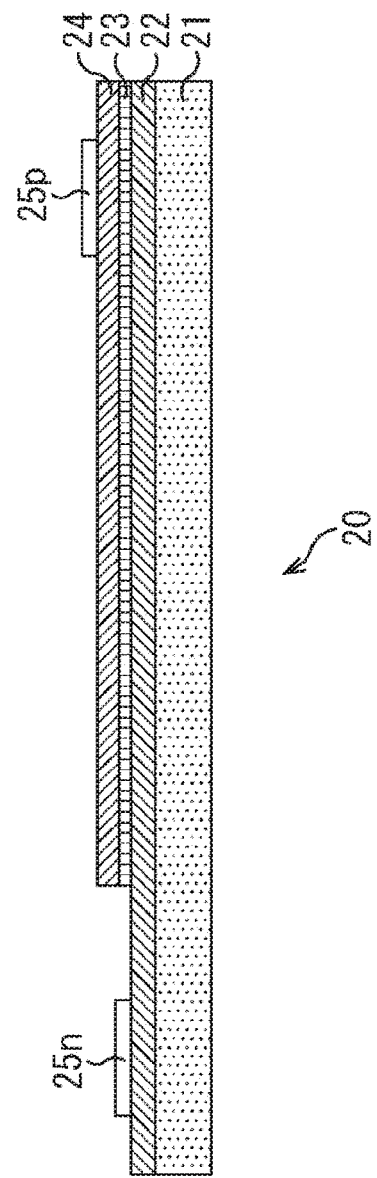
FIG. 2 is a cross-sectional view illustrating a general configuration example of a light emitting element.

FIG. 2 is a cross-sectional view illustrating a general configuration example of the blue LED element which is an example of a light emitting element before integration.

A blue LED element 20 is obtained by stacking an n layer 22, a light emitting layer 23, and a p layer 24 on sapphire glass 21 as a support substrate. For example, GaN, GaAs, SiC and the like may be used as materials of the n layer 22 and the p layer 24. Wire bonding pads 25n and 25p are formed on the n layer 22 and the p layer 24, respectively.

The sapphire glass (SiN glass) 21 has higher strength than that of the SiO glass used as the cover glass 11 of the solid-state imaging element 10, and is polished to approximately 70 μm in a manufacturing process.

In the blue LED element 20, blue light is output from the light emitting layer 23 by application of voltage from the n side wire bonding pad 25n and the p side wire bonding pad 25p. Note that an irradiation direction of the blue light may be adjusted to either the sapphire glass 21 side or the opposite side.

First Embodiment

Figure 3:
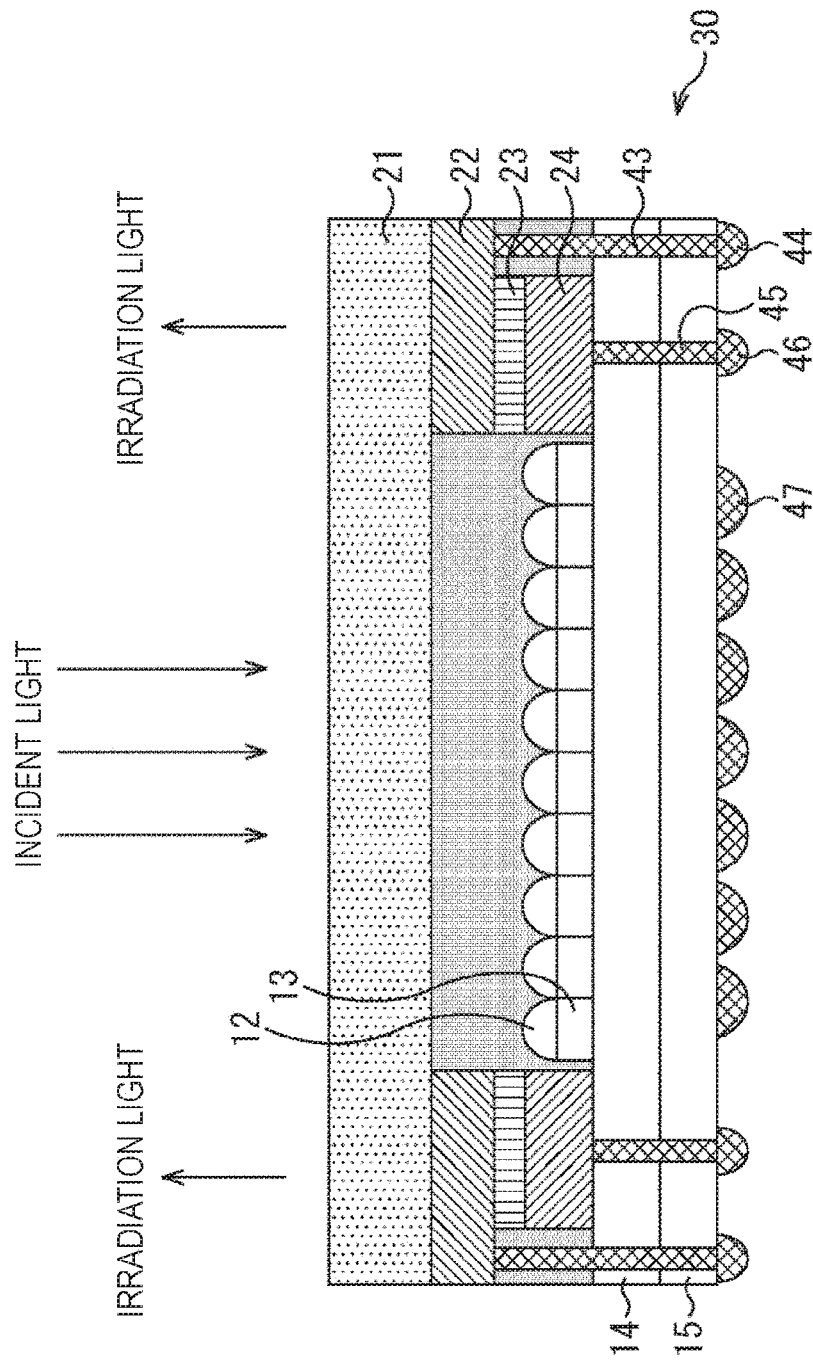
FIG. 3 is a cross-sectional view illustrating a configuration example of a CSP being a first embodiment.

Next, FIG. 3 is a cross-sectional view illustrating a configuration example of a chip size package obtained by integrating a solid-state imaging element and a blue LED element by a wafer level chip size package (WCSP) manufacturing method being a first embodiment of the present disclosure.

Hereinafter, out of components of the CSP, the same reference sign is assigned to a component common to that of the above-described solid-state imaging element 10 and blue LED element 20, so that the description thereof is omitted as appropriate.

A CSP 30 being the first embodiment is manufactured by the WCSP manufacturing method of bonding a substrate on which the solid-state imaging elements 10 for a plurality of chips are formed to a substrate on which the blue LED elements 20 for a plurality of chips are formed.

The CSP 30 is formed using sapphire glass 21 being a component of the blue LED element 20 as a support substrate such that the sapphire glass 21 also serves as a cover glass of the solid-state imaging element 10.

By using the sapphire glass 21 having higher strength than that of SiO glass, it is possible to make the cover glass thinner and make an entire CSP 30 smaller in height (make a module compact).

The solid-state imaging element 10 of the CSP 30 is connected to the outside via a solder ball 47. Voltage is applied to the blue LED element 20 of the CSP 30 via a solder ball 44 and a VIA (penetrating electrode) 43, and via a solder ball 46 and a VIA 45.

FIGS. 4A, 4B, 4C, 4D, 4E, 4F, 4G, and 4H are views for illustrating a manufacturing process of the CSP 30 by the WCSP manufacturing method.

In a first process, as illustrated in A of the drawing, the substrate on which the blue LED elements 20 for a plurality of chips are adjacently formed with a scribe region provided therebetween is prepared. In a next process, as illustrated in B of the drawing, resist patterning is performed for applying a protective film 41 so as to cover one to be integrated with the solid-state imaging element 10 out of the blue LED elements 20 for a plurality of chips on the substrate.

In a next process, as illustrated in C of the drawing, etching is performed to scrape off the blue LED element (n layer 22, light emitting layer 23, and p layer 24) not covered with the protective film 41, and thereafter the protective film 41 is removed as illustrated in D of the drawing.

This etching may be either dry etching or wet etching. Furthermore, when a laser lift-off manufacturing method is selectively performed instead of the etching, the removed blue LED element may be diverted to other applications.

In parallel to the above-described processes, as illustrated in E of the drawing, a substrate on which the solid-state imaging elements 10 for a plurality of chips are adjacently formed with a scribe region provided therebetween is prepared. However, it is assumed that a cover glass 11 and a solder ball 16 are not formed on the solid-state imaging element 10.

In a next process, as illustrated in F of the drawing, sealing resin 42 is applied onto the substrate on the side of the solid-state imaging element 10, and as illustrated in G of the drawing, the substrate on the side of the blue LED element 20 is bonded to the substrate on the side of the solid-state imaging element 10 such that the blue LED element (n layer 22, light emitting layer 23, and p layer 24) is buried into the sealing resin 42.

Moreover, as illustrated in H of the drawing, after forming the VIAs 43 and 45 from the wiring layer 15 side to the n layer 22 and the p layer 24 of the blue LED element 20, respectively, the solder balls 44 and 46 are formed on a surface of the wiring layer 15. Furthermore, the solder ball 47 is formed also on a bottom of the solid-state imaging element 10.

Finally, both the bonded substrates are divided into a plurality of CSPs 30 in a singulation process.

In the singulation process, the sapphire glass 21 is first ground to a desired thickness. Note that this process may be omitted in a case where the sapphire glass 21 is already polished to the desired thickness. Next, the scribe region between the CSPs 30 is cut by dry etching, laser cutting, or dicing from the wiring layer 15 side (lower side in the drawing) to the sapphire glass 21 sequentially. Note that this cutting may be temporarily stopped for each layer or may be carried out continuously. Furthermore, it is also possible to cut from the wiring layer 15 side to the p layer 24 sequentially and cut the sapphire glass 21 from the opposite side (the upper side in the drawing). Moreover, diamond scribing and breaking may be adopted when cutting the sapphire glass 21.

Second Embodiment

Figure 5:
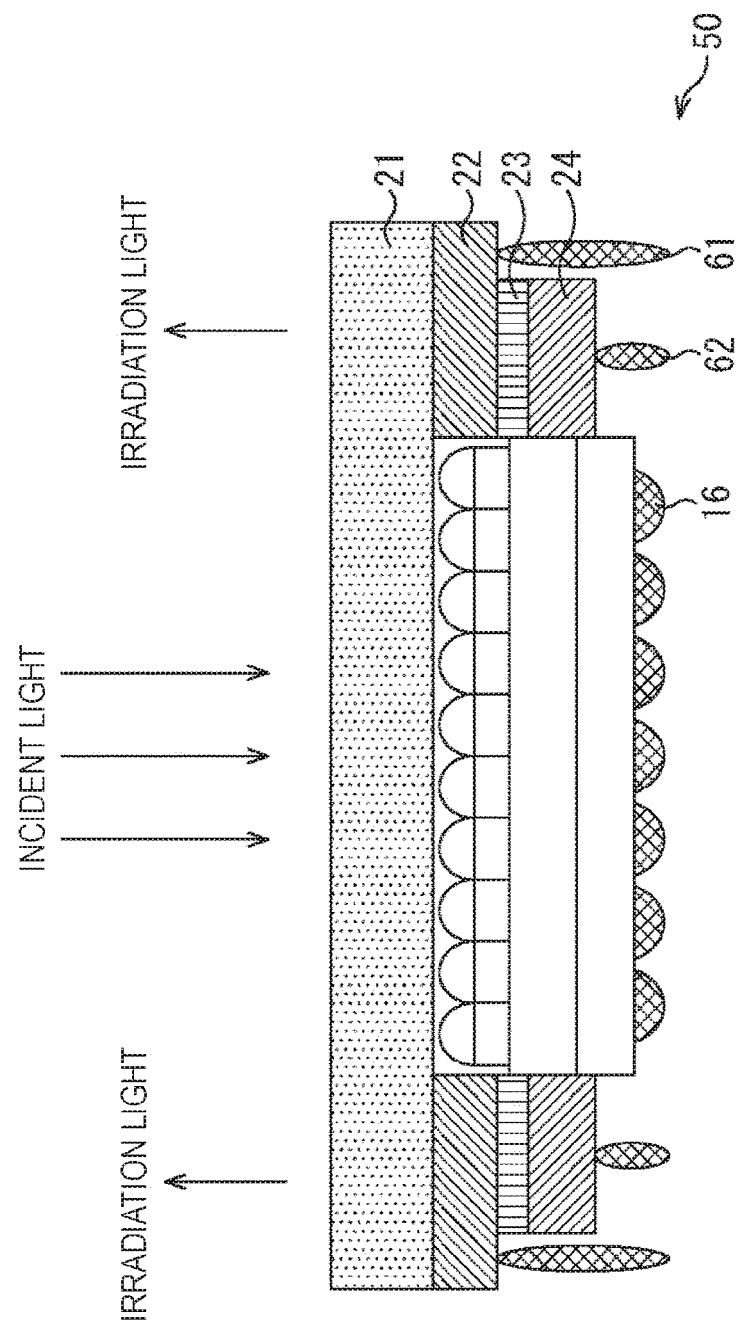
FIG. 5 is a cross-sectional view illustrating a configuration example of a CSP being a second embodiment.

Next, FIG. 5 is a cross-sectional view illustrating a configuration example of a CSP obtained by integrating a solid-state imaging element and a blue LED element by a chip on wafer (COW) manufacturing method being a second embodiment of the present disclosure.

A CSP 50 being the second embodiment is manufactured by the COW manufacturing method of stacking a CSP solid-state imaging element 10 on a substrate on which blue LED elements 20 for a plurality of chips are formed.

The CSP 50 is formed using sapphire glass 21 being a component of the blue LED element 20 as a support substrate such that the sapphire glass 21 also serves as a cover glass of the solid-state imaging element 10.

By using the sapphire glass 21 having high strength, it is possible to make the cover glass thinner and make an entire CSP 50 smaller in height (make a module compact).

The solid-state imaging element 10 of the CSP 50 is connected to outside via a solder ball 16. Voltage is applied to the blue LED element 20 of the CSP 50 via solder balls 61 and 62.

Figure 6A:
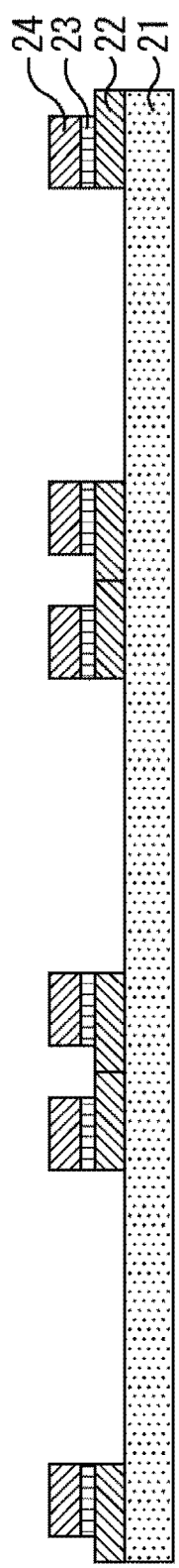
FIGS. 6A, 6B, and 6C are views for illustrating a manufacturing process of the CSP being the second embodiment.
Figure 6B:
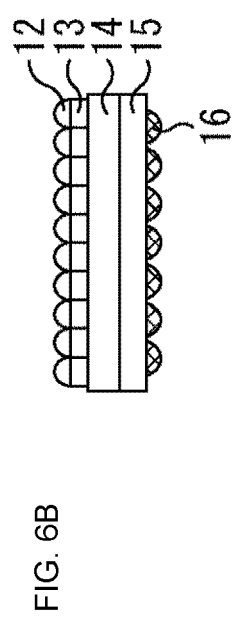
Figure 6C:
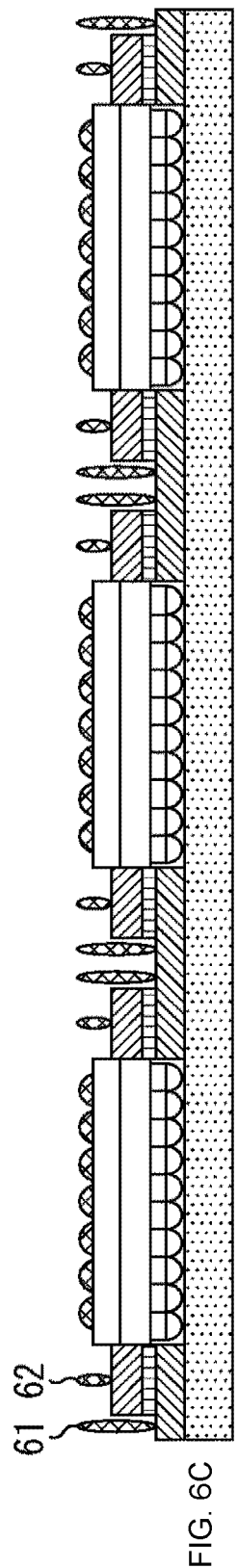

FIGS. 6A, 6B, and 6C are views for illustrating a manufacturing process of the CSP 50 by the COW manufacturing method.

Figure 4A:
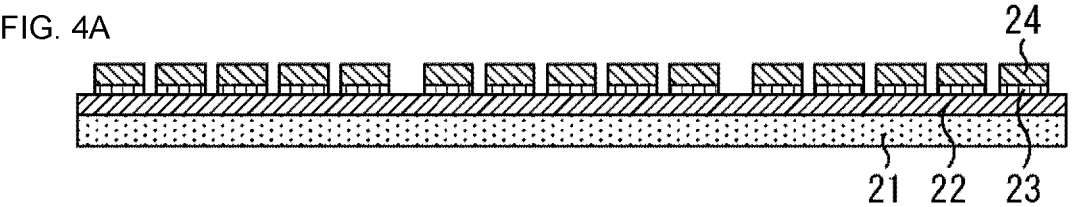
FIGS. 4A, 4B, 4C, 4D, 4E, 4F, 4G, and 4H are views for illustrating a manufacturing process of the CSP being the first embodiment.
Figure 4B:
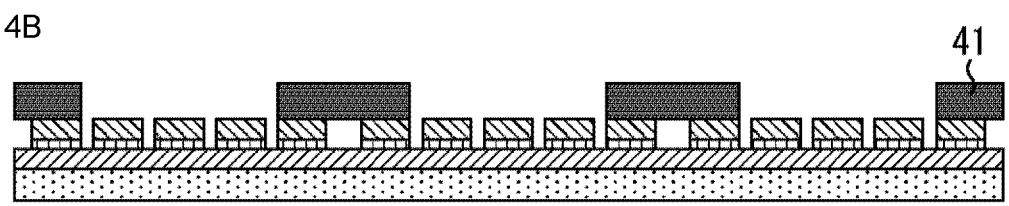
Figure 4C:
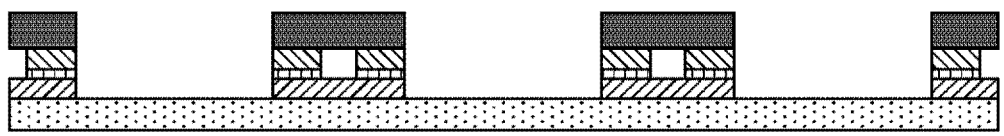
Figure 4D:
Figure 4E:
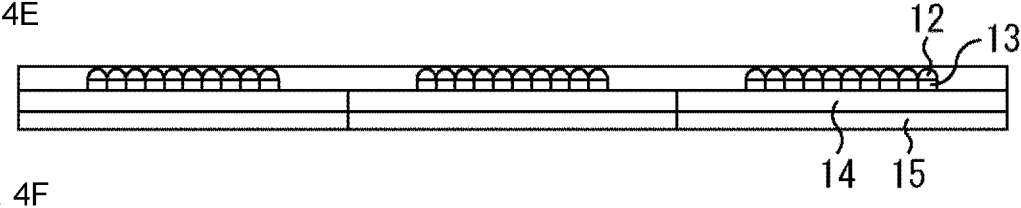
Figure 4F:
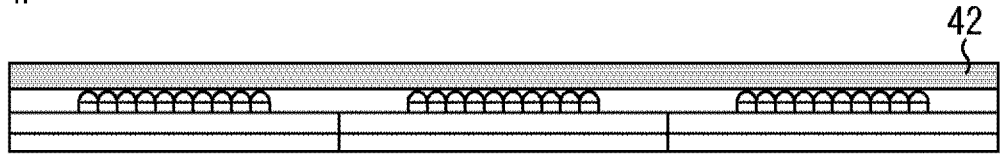
Figure 4G:
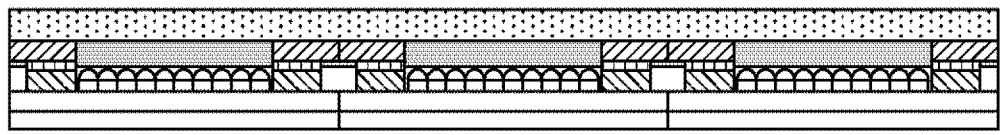

In a first process, as illustrated in FIG. 4A, a substrate on which only the blue LED element to be integrated with the solid-state imaging element 10 is left obtained in the above-described processes in FIGS. 4A, 4B, 4C, and 4D is prepared.

In parallel to the above-described process, as illustrated in B of the drawing, the CSP solid-state imaging element 10 is prepared. However, it is assumed that a cover glass 11 is not formed on the solid-state imaging element 10.

In a next process, as illustrated in C of the drawing, the CSP solid-state imaging element 10 is placed on the substrate of the blue LED element 20, and the solder balls 61 and 62 are formed so as to be in contact with an n layer 22 and a p layer 24 of the blue LED element 20, respectively.

Finally, the substrate on which the solid-state imaging element 10 is placed is divided into a plurality of CSPs 50 by a singulation process. This singulation process is similar to that of the case of the CSP 30 described above, so that the description thereof is omitted.

Third Embodiment

Next, FIG. 7 is a cross-sectional view illustrating a configuration example of a CSP obtained by integrating a solid-state imaging element and a blue LED element by a COW manufacturing method being a third embodiment of the present disclosure.

A CSP 70 being the third embodiment is manufactured by the COW manufacturing method of stacking a chip of a solid-state imaging element 10 which is not packaged on a substrate on which blue LED elements 20 for a plurality of chips are formed.

The CSP 70 is formed using sapphire glass 21 being a component of the blue LED element 20 as a support substrate such that the sapphire glass 21 also serves as a cover glass of the solid-state imaging element 10.

By using the sapphire glass 21 having high strength as the support substrate of the CSP 50, it is possible to make the cover glass thinner and make an entire CSP 70 smaller in height (make a module compact).

The solid-state imaging element 10 of the CSP 70 is connected to the outside via a wire 81. Voltage is applied to the blue LED element 20 of the CSP 70 via wires 82 and 83.

Figure 8A:
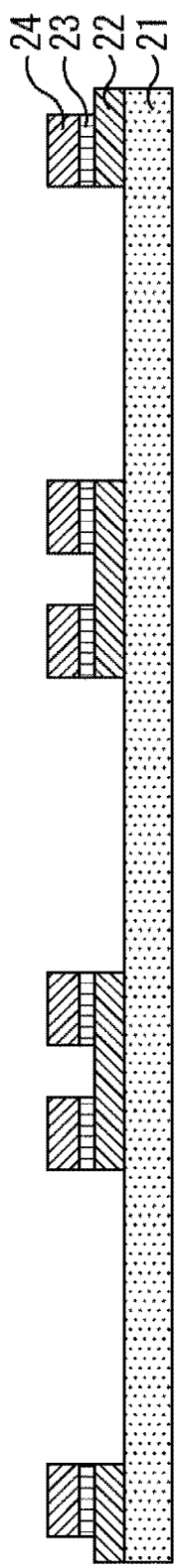
FIGS. 8A, 8B, and 8C are views for illustrating a manufacturing process of the CSP being the third embodiment.
Figure 8B:
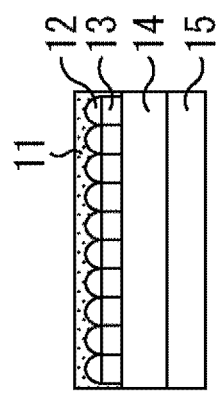
Figure 8C:
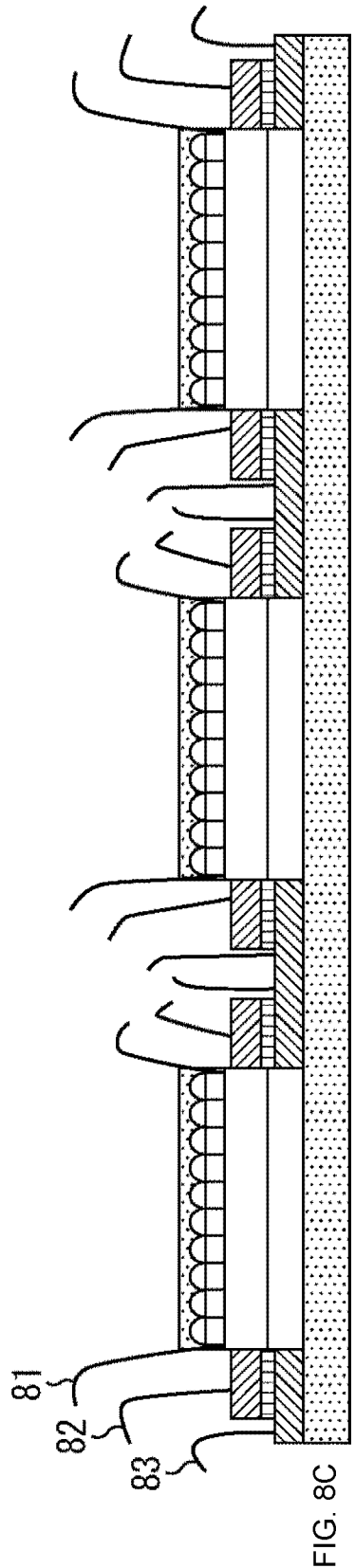

FIGS. 8A, 8B, and 8C are views for illustrating a manufacturing process of the CSP 70 by the COW manufacturing method.

In a first process, as illustrated in A of the drawing, a substrate on which only the blue LED element to be integrated with the solid-state imaging element 10 is left obtained in the above-described processes in FIGS. 4A, 4B, 4C, and 4D is prepared.

In parallel to the above-described process, as illustrated in B of the drawing, the chip of the solid-state imaging element 10 which is not packaged is prepared. However, it is assumed that a solder ball 16 is not formed on the solid-state imaging element 10.

In a next process, as illustrated in C of the drawing, the chip of the solid-state imaging element 10 is placed on the substrate on the blue LED element 20 side and the wire 81 is connected thereto, and moreover, the wires 82 and 83 are connected to an n layer 22 and a p layer 24 of the blue LED element 20, respectively.

Finally, the substrate on which the solid-state imaging element 10 is placed is divided into a plurality of CSPs 70 by a singulation process. This singulation process is similar to that of the case of the CSP 30 described above, so that the description thereof is omitted.

Fourth Embodiment

Figure 9:
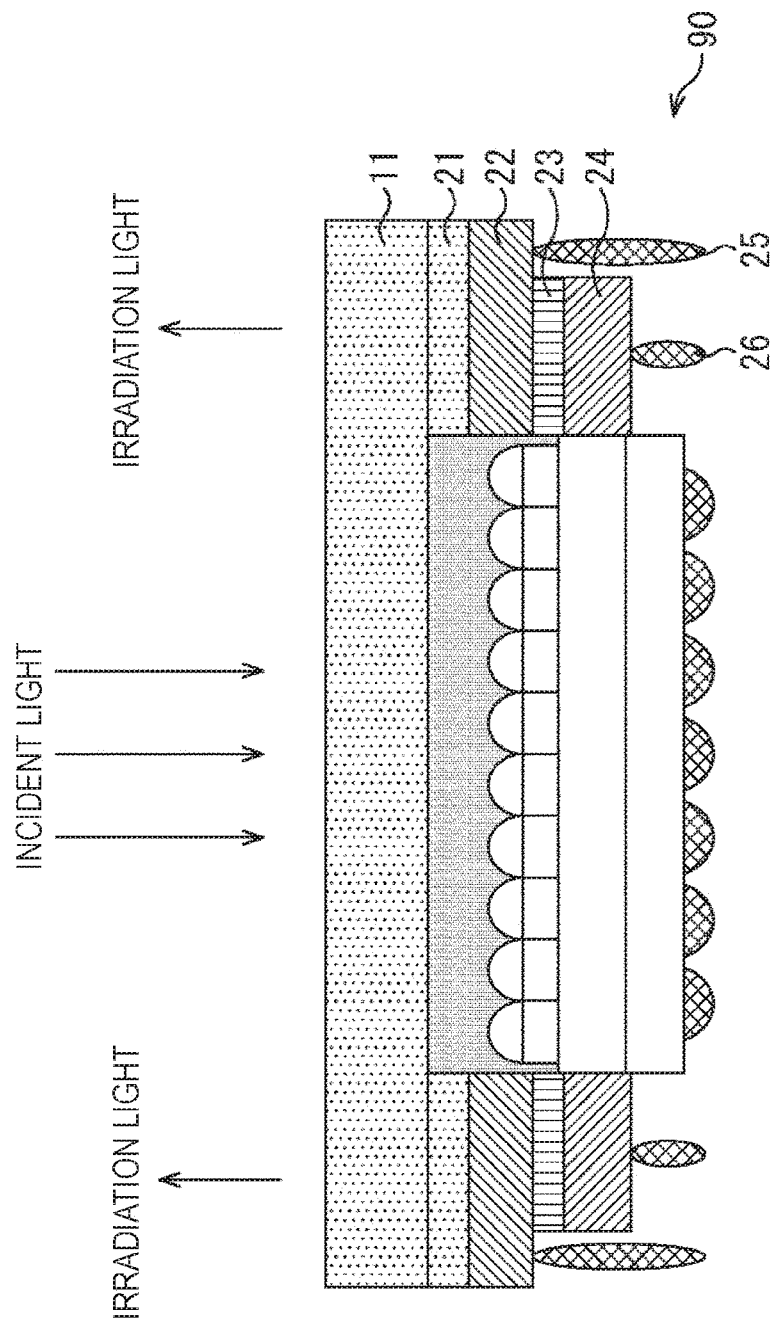
FIG. 9 is a cross-sectional view illustrating a configuration example of a CSP being a fourth embodiment.
Figure 10A:
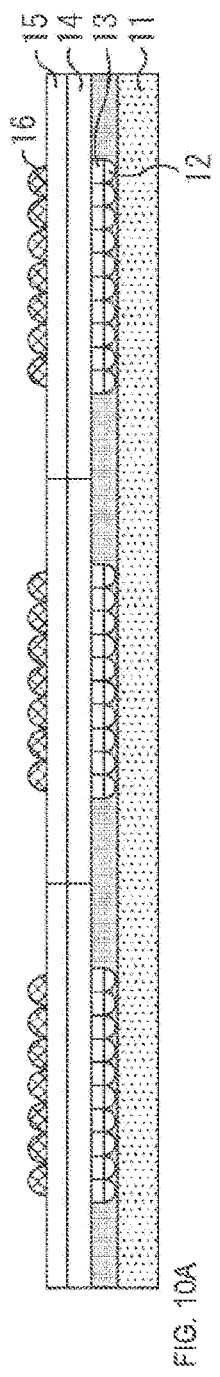
FIGS. 10A, 10B, 10C, and 10D are views for illustrating a manufacturing process of the CSP being the fourth embodiment.
Figure 10B:
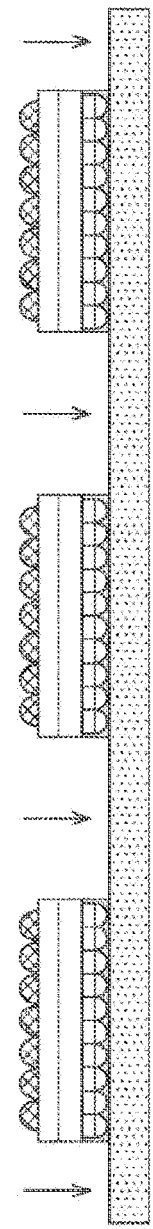
Figure 10C:
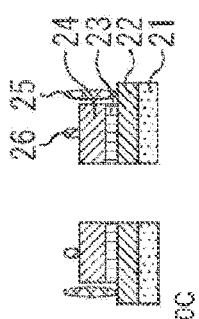
Figure 10D:
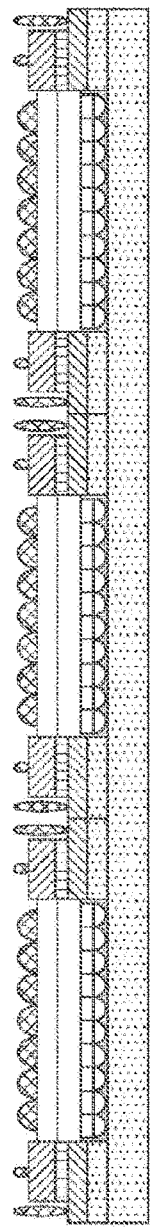

Next, FIG. 9 is a cross-sectional view illustrating a configuration example of a CSP obtained by integrating a solid-state imaging element and a blue LED element by a COW manufacturing method being a fourth embodiment of the present disclosure.

A CSP 90 being the fourth embodiment is manufactured by the COW manufacturing method of stacking a CSP blue LED element 20 on a substrate on which solid-state imaging elements 10 for a plurality of chips are formed.

The CSP 90 is formed using a cover glass 11 being a component of the solid-state imaging element 10 as a support substrate.

The solid-state imaging element 10 of the CSP 90 is connected to the outside via a solder ball 16. Voltage is applied to the blue LED element 20 of the CSP 90 via solder balls 25 and 26.

FIGS. 10A, 10B, 10C and 10D are views for illustrating a manufacturing process of the CSP 90 by the COW manufacturing method.

In a first process, as illustrated in A of the drawing, the substrate on which the solid-state imaging elements 10 for a plurality of chips are formed is prepared. In a next process, as illustrated B of the drawing, in order to provide a space in which the blue LED element 20 is placed, a wiring layer 15 and the like between the solid-state imaging elements 10 on the substrate is removed.

In parallel to the above-described processes, as illustrated in C of the drawing, the CSP blue LED element 20 is prepared. In a next process, as illustrated in D of the drawing, the CSP blue LED element 20 is placed in the space provided on the substrate of the solid-state imaging element 10.

Finally, the substrate on which the blue LED element 20 is placed is divided into a plurality of CSPs 90 in a singulation process. This singulation process is similar to that of the case of the CSP 30 described above, so that the description thereof is omitted.

In the first to fourth embodiments described above, since the solid-state imaging element 10 and the blue LED element 20 are arranged so as to be adjacent to each other, a phenomenon that the irradiation light of the blue LED element 20 is reflected on the solid-state imaging element 10 (hereinafter, referred to as "stray light") might occur. Therefore, a configuration for suppressing the occurrence of the stray light is also proposed.

Fifth Embodiment

Figure 11:
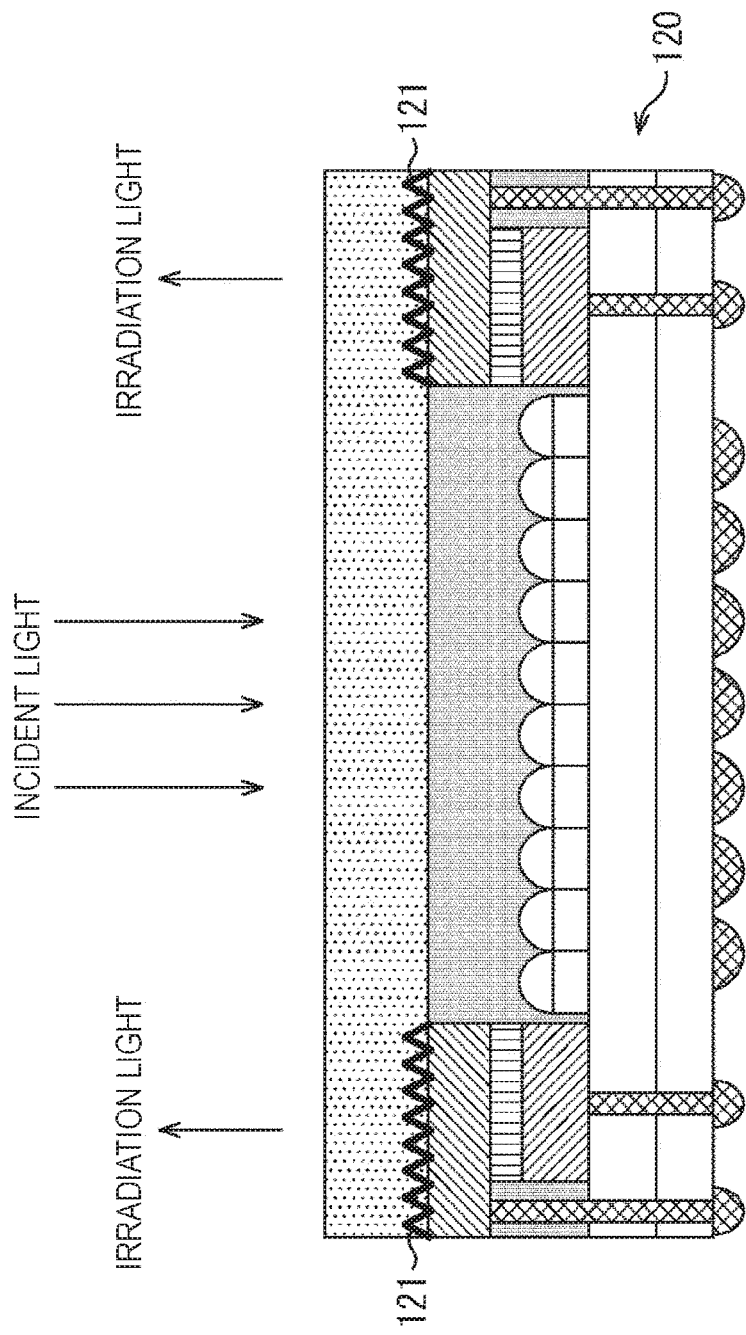
FIG. 11 is a cross-sectional view illustrating a configuration example of a CSP being a fifth embodiment.

FIG. 11 is a cross-sectional view illustrating a configuration example of a CSP obtained by integrating a solid-state imaging element and a blue LED element being a fifth embodiment of the present disclosure.

A CSP 120 being the fifth embodiment is obtained by adding/forming a moth-eye processed portion 121 on sapphire glass 21 in a blue LED element 20 of a CSP 30 being the first embodiment.

The moth-eye processed portion 121 is formed by etching on the sapphire glass 21 before forming an n layer 22 on the sapphire glass 21.

In the CSP 120, the moth-eye processed portion 121 is formed, directivity of light emitted from the blue LED element 20 may be increased, so that it is possible to suppress the irradiation light from straying in a chip.

Note that it is also possible to apply the moth-eye process on the sapphire glass 21 with which a solid-state imaging element 10 of the CSP 120 is brought into contact; in this case, it is expected that receiving sensitivity of the solid-state imaging element 10 is also improved.

Sixth Embodiment

Figure 12:
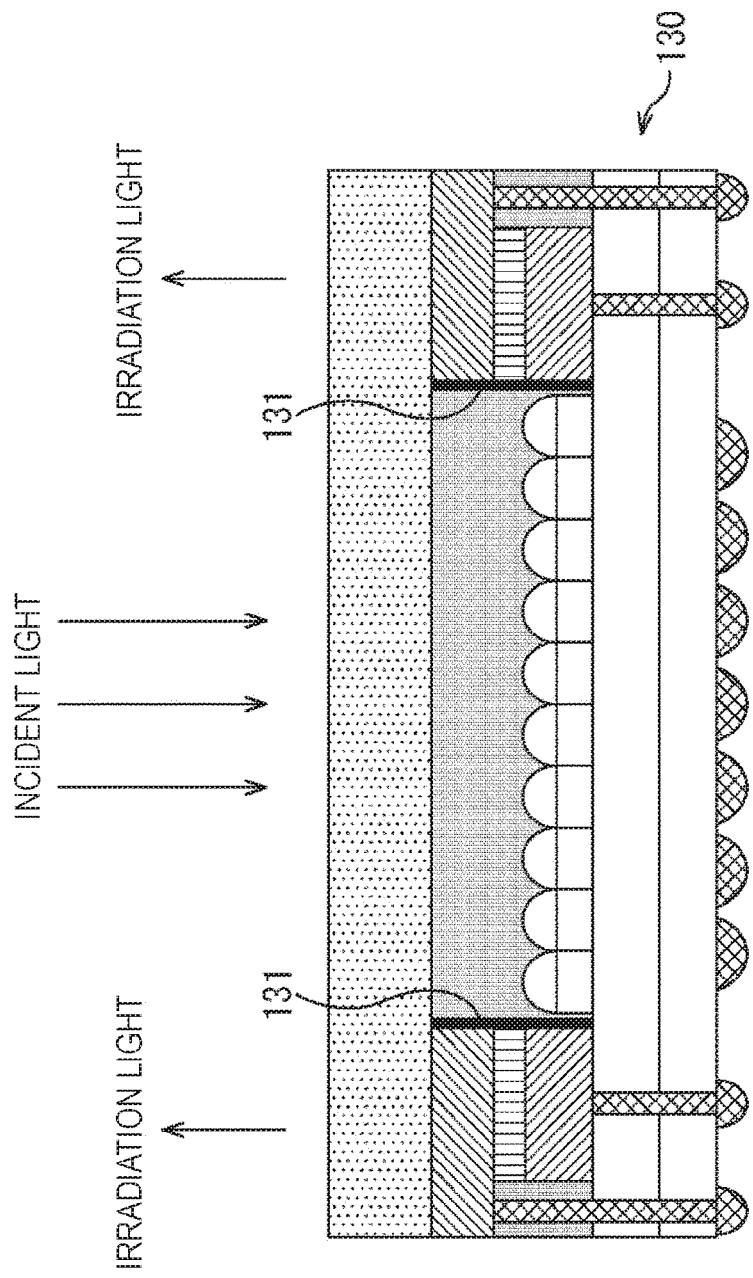
FIG. 12 is a cross-sectional view illustrating a configuration example of a CSP being a sixth embodiment.

FIG. 12 is a cross-sectional view illustrating a configuration example of a CSP obtained by integrating a solid-state imaging element and a blue LED element being a sixth embodiment of the present disclosure.

A CSP 130 being the sixth embodiment is obtained by adding/forming a light shielding wall 131 at a boundary between a solid-state imaging element 10 and a blue LED element 20 of a CSP 30 being the first embodiment.

The light shielding wall 130 is formed on a side of a substrate on which the blue LED element 20 is formed before this is bonded to a substrate on which the solid-state imaging element 10 is formed.

In the light shielding wall 131, for example, a metal material such as Al, Au, Co, Ni, Cu, W, and Ti, an inorganic material such as SiO, SiN, and SiON, an organic material such as a color filter, a deflecting element such as crystal and liquid crystal, or a combination thereof may be used.

In the CSP 130, since the light shielding wall 131 is formed, it is possible to suppress the irradiation light from the blue LED element 20 from being directly incident on the solid-state imaging element 10.

Seventh Embodiment

Figure 13:
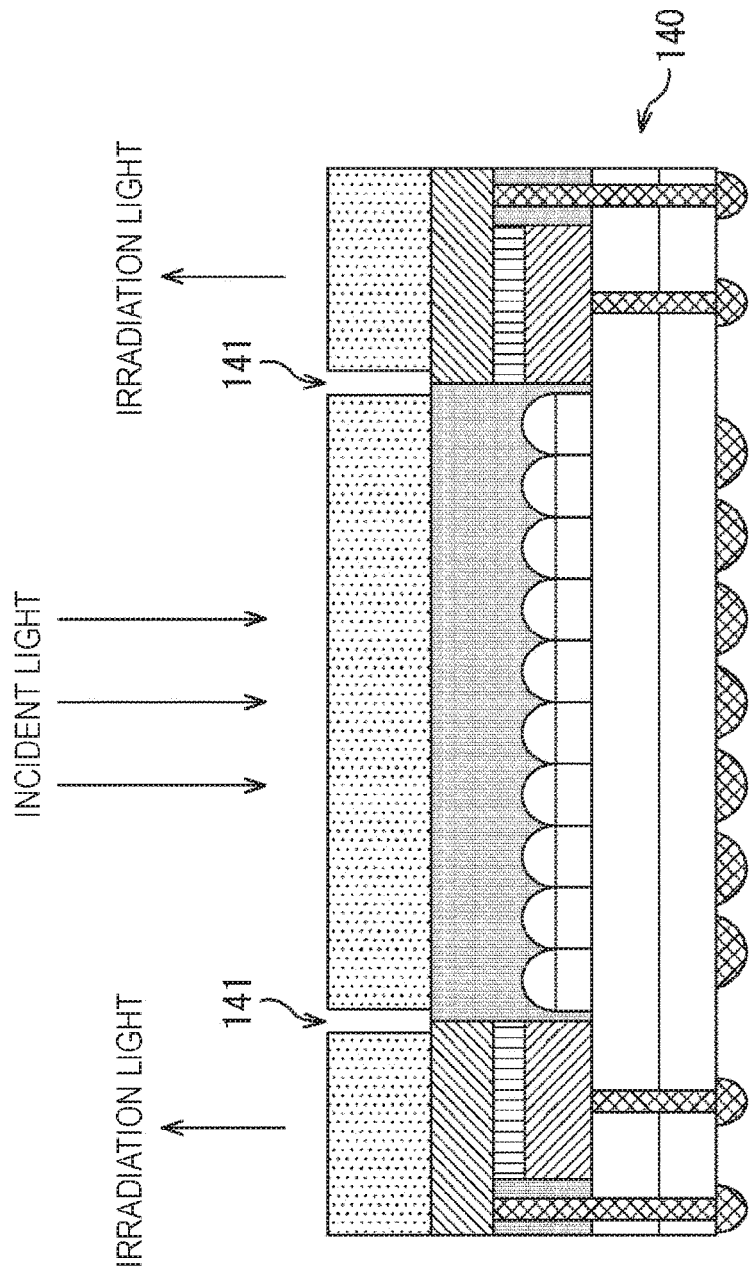
FIG. 13 is a cross-sectional view illustrating a configuration example of a CSP being a seventh embodiment.

FIG. 13 is a cross-sectional view illustrating a configuration example of a CSP obtained by integrating a solid-state imaging element and a blue LED element being a seventh embodiment of the present disclosure.

A CSP 140 being the seventh embodiment is obtained by adding/forming a light shielding groove 141 in sapphire glass 21 above a boundary between a solid-state imaging element 10 and a blue LED element 20 of a CSP 30 being the first embodiment.

Figure 4H:
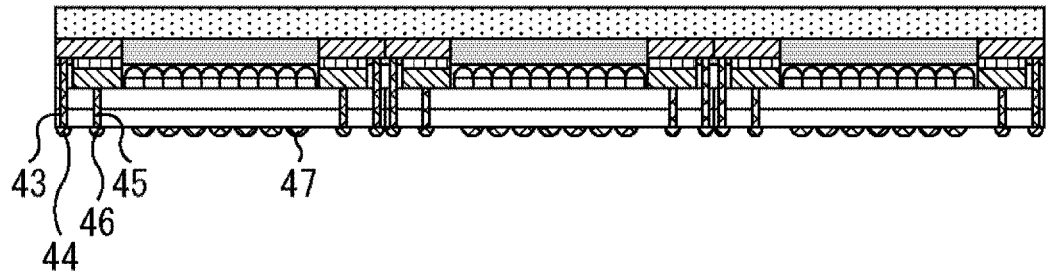

The light shielding groove 141 may be formed in a state before singulation illustrated in FIG. 4H, or after that. However, a processing amount (width and depth) of the light shielding groove 141 is trade-off between a risk that the sapphire glass 21 breaks during conveyance and a light shielding performance. Since the breaking risk of the sapphire glass 21 decreases in a case of forming the light shielding groove 141 after singulation, it is possible to provide the same together with a light shielding wall 130 of a CSP 130 being the sixth embodiment described above, and the light shielding wall 130 and the light shielding groove 141 may be continuously formed.

The light shielding groove 141 may remain as a void or may be filled with a light shielding material similar to that of the light shielding wall 130 of the CSP 130 being the sixth embodiment described above.

In the CSP 140, since the light shielding groove 141 is formed, it is possible to suppress irradiation light from the blue LED element 20 from being reflected in the sapphire glass 21 to be incident on the solid-state imaging element 10.

Eighth Embodiment

Figure 14:
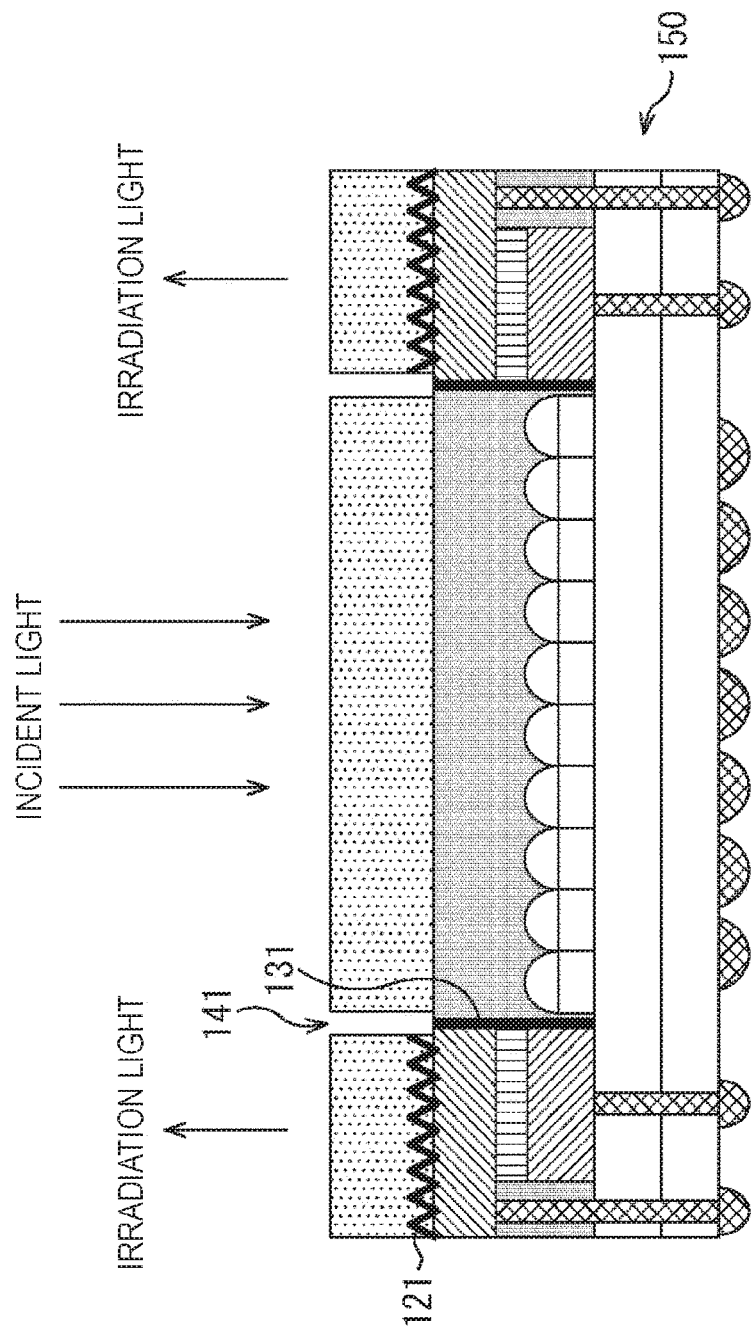
FIG. 14 is a cross-sectional view illustrating a configuration example of a CSP being an eighth embodiment.

FIG. 14 is a cross-sectional view illustrating a configuration example of a CSP obtained by integrating a solid-state imaging element and a blue LED element being an eighth embodiment of the present disclosure.

A CSP 150 being the eighth embodiment is obtained by providing the above-described moth-eye processed portion 121, light shielding wall 131, and light shielding groove 141 on the CSP 30 being the first embodiment.

In the CSP 150, since the moth-eye processed portion 121, the light shielding wall 131, and the light shielding groove 141 are formed, stray light in a chip may be suppressed.

<Variation>

Although not illustrated, the above-described moth-eye processed portion 121, light shielding wall 131, or light shielding groove 141 may be added/formed individually or in an appropriately combined manner on the CSPs 30, 50, 70, and 90 being the first to fourth embodiments.

Furthermore, in the first to eighth embodiments described above, the light emitting element to be integrated with the solid-state imaging element is the blue LED element, but it is also possible to combine an infrared LED element, an ultraviolet LED element, a laser element and the like instead of the blue LED element or in addition to the blue LED element.

Application Example of First to Eighth Embodiments

A CSP being the first to eighth embodiments may be applied to various electronic devices.

For example, this may be applied to an electronic device which performs indocyanine green (ICG) (fluorescent contrast radiography) observation in medical applications. In the ICG observation, since excitation light is of 760 nm and fluorescence is of 850 nm, it is possible to use a light emitting element which outputs light of a wavelength of 760 nm.

In the ICG observation, it is desirable that spectral ripple is small because of a low sensitivity narrow wavelength band. The spectral ripple is generated by interference on reflective interface, but the spectral ripple may be significantly suppressed in the CSP of this embodiment. Specifically, for example, by designing an antireflection film having a film thickness of d=wavelength $\lambda/(4 \times \text{refractive index n})$ by using a material of an intermediate refractive index between air and sapphire glass 21 having a refractive index of n=1 to 1.7 on an outermost surface, the ICG wavelength ripple may be minimized.

Furthermore, in a case of the CSP of this embodiment, it is possible to simultaneously form the antireflection film which is conventionally processed individually for the solid-state imaging element and the light emitting element.

Figure 15:
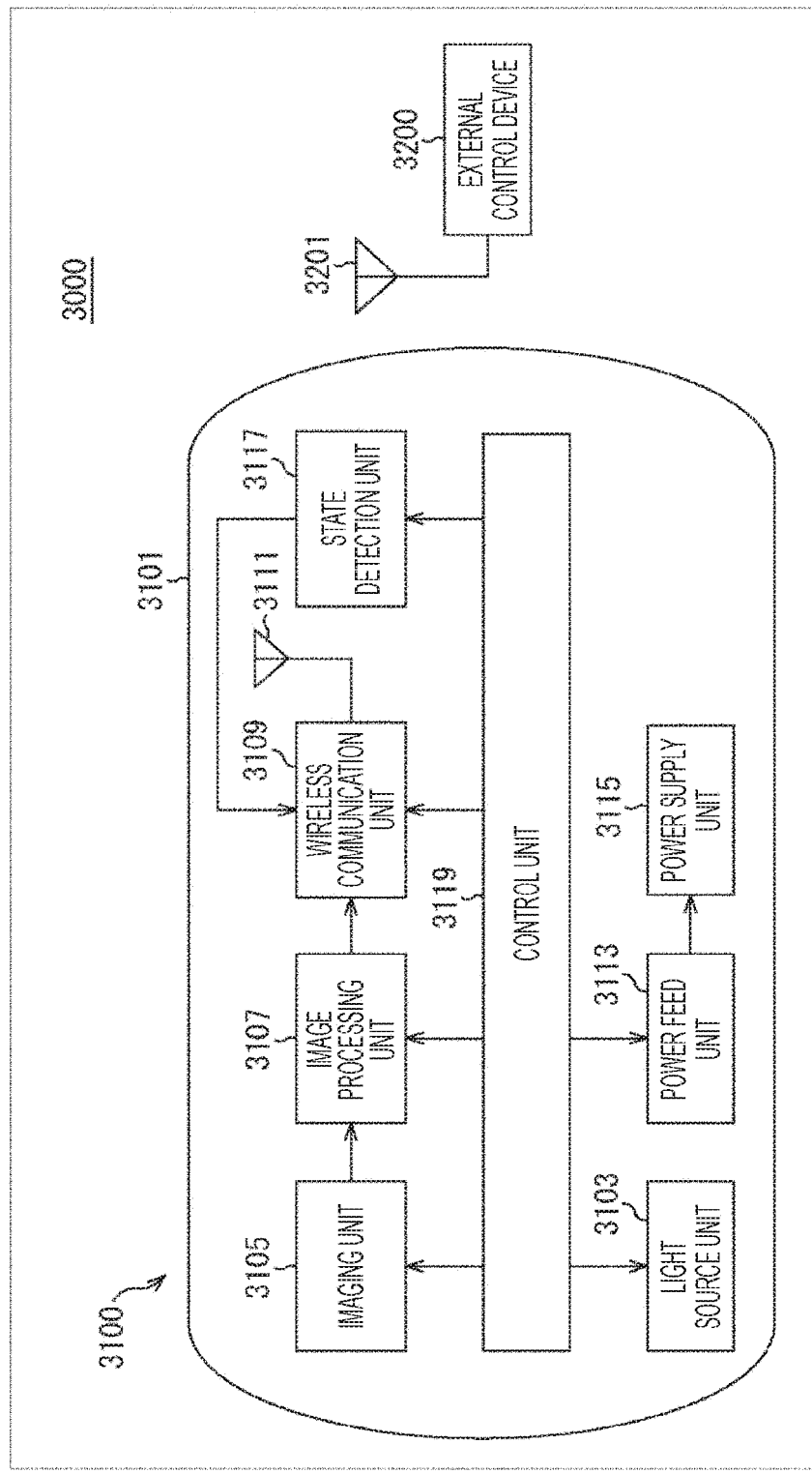
FIG. 15 is a block diagram illustrating a configuration example of an in-vivo information obtaining system including a capsule endoscope to which the first to eighth embodiments are applied.

Next, FIG. 15 illustrates a schematic configuration example of an in-vivo information obtaining system of a patient using a capsule endoscope in a case where the CSP being the first to eighth embodiments is applied to the capsule endoscope.

An in-vivo information obtaining system 3000 includes a capsule endoscope 3100 which is swallowed by a patient at the time of examination and an external control device 3200 which comprehensively controls operation of the in-vivo information obtaining system 3000.

The capsule endoscope 3100 has an imaging function and a wireless communication function and sequentially takes images in organs (hereinafter, also referred to as in-vivo images) at a predetermined interval while moving in the organs such as the stomach and the intestine by peristaltic movement or the like until naturally discharged from the patient, and sequentially wirelessly transmits information regarding the in-vivo images to the external control device 3200 outside the body.

The external control device 3200 generates image data for displaying the in-vivo image on a display device (not illustrated) on the basis of the received information regarding the in-vivo image.

In the in-vivo information obtaining system 3000, it is possible to obtain as needed the image of the inside the patient's body from when the capsule endoscope 3100 is swallowed until this is discharged in this manner.

Configurations and functions of the capsule endoscope 3100 and the external control device 3200 are described in detail.

The capsule endoscope 3100 has functions of a light source unit 3103, an imaging unit 3105, an image processing unit 3107, a wireless communication unit 3109, a power feed unit 3113, a power supply unit 3115, a state detection unit 3117, and a control unit 3119 in a capsule-shaped casing 3101.

The light source unit 3103 irradiates an imaging visual field of the imaging unit 3105 with light. The imaging unit 3105 receives reflected light of the light applied to body tissue being an observation target and photoelectrically converts the same to generate an electric signal corresponding to the observation light, that is, an image signal corresponding to an observation image. The image signal generated by the imaging unit 3105 is provided to the image processing unit 3107.

The CSP being the first to eighth embodiments is used as the light source unit 3103 and the imaging unit 3105.

The image processing unit 3107 includes a processor such as a central processing unit (CPU) and a graphics processing unit (GPU), and performs various types of signal processing on the image signal generated by the imaging unit 3105. The signal processing may be minimum processing (such as image data compression, frame rate conversion, data rate conversion and/or format conversion, for example) for transmitting the image signal to the external control device 3200. Since the image processing unit 3107 is configured to perform only requisite minimum processing, the image processing unit 3107 may be realized with a smaller size and lower power consumption, so that this is preferable as the capsule endoscope 3100. However, in a case where there is a space in the casing 3101 and extra power consumption, it is possible to perform further signal processing (for example, noise removal processing, other high image quality processing and the like) in the image processing unit 3107.

The image processing unit 3107 provides the image signal subjected to the signal processing to the wireless communication unit 3109 as RAW data. Note that in a case where information regarding a state (movement, attitude and the like) of the capsule endoscope 3100 is obtained by the state detection unit 3117, the wireless communication unit 3109 may provide the image signal to the wireless communication unit 3109 in association with the information. As a result, it is possible to associate a position in the body in which the image is taken, an imaging direction of the image and the like with the taken image.

The wireless communication unit 3109 includes a communication device capable of transmitting/receiving various types of information to/from the external control device 3200. The communication device includes an antenna 3111, a processing circuit for performing modulation processing and the like for transmitting and receiving signals and the like. The wireless communication unit 3109 performs predetermined processing such as the modulation processing on the image signal subjected to the signal processing by the image processing unit 3107 and transmits the image signal to the external control device 3200 via the antenna 3111. Furthermore, the wireless communication unit 3109 receives a control signal regarding drive control of the capsule endoscope 3100 from the external control device 3200 via the antenna 3111. The wireless communication unit 3109 provides the received control signal to the control unit 3119.

The power feed unit 3113 includes an antenna coil for power reception, a power regeneration circuit for regenerating electric power from current generated in the antenna coil, a booster circuit and the like. In the power feed unit 3113, electric power is generated using a so-called non-contact charging principal. Specifically, a magnetic field (electromagnetic wave) of a predetermined frequency is externally given to an antenna coil of the power feed unit 3113, so that induced electromotive force is generated in the antenna coil. The electromagnetic wave may be a carrier wave transmitted from the external control device 3200 via an antenna 3201, for example. Electric power is regenerated from the induced electromotive force by the power regeneration circuit, and electric potential thereof is appropriately adjusted in a boosting circuit, so that electric power for storage is generated. The electric power generated by the power feed unit 3113 is stored in the power supply unit 3115.

The power supply unit 3115 includes a secondary battery and stores electric power generated by the power feed unit 3113. However, in FIG. 15, an arrow or the like indicating a destination of the electric power from the power supply unit 3115 is not illustrated.

The state detection unit 3117 includes a sensor for detecting the state of the capsule endoscope 3100 such as an acceleration sensor and/or a gyro sensor. The state detection unit 3117 may obtain the information regarding the state of the capsule endoscope 3100 from a detection result by the sensor. The state detection unit 3117 provides the obtained information regarding the state of the capsule endoscope 3100 to the image processing unit 3107. As described above, in the image processing unit 3107, the information regarding the state of the capsule endoscope 3100 may be associated with the image signal.

The control unit 3119 is configured by a processor such as a CPU, and comprehensively controls operation of the capsule endoscope 3100 by operating according to a predetermined program. The control unit 3119 appropriately controls drive of the light source unit 3103, the imaging unit 3105, the image processing unit 3107, the wireless communication unit 3109, the power feed unit 3113, the power supply unit 3115, and the state detection unit 3117 according to the control signal transmitted from the external control device 3200, thereby realizing the function in each unit as described above.

The external control device 3200 may be a processor such as a CPU and a GPU, or a microcomputer, a control substrate or the like on which a processor and a storage element such as a memory are mixedly mounted. The external control device 3200 includes the antenna 3201 and is configured to be able to transmit and receive various types of information to and from the capsule endoscope 3100 via the antenna 3201.

Specifically, the external control device 3200 controls the operation of the capsule endoscope 3100 by transmitting the control signal to the control unit 3119 of the capsule endoscope 3100. For example, an irradiation condition of light to the observation target in the light source unit 3103 might be changed by the control signal from the external control device 3200. Furthermore, an imaging condition (for example, a frame rate, exposure value and the like in the imaging unit 3105) might be changed by the control signal from the external control device 3200. Furthermore, content of the processing in the image processing unit 3107 and a condition (for example, transmission interval, the number of transmitted images and the like) for the wireless communication unit 3109 to transmit the image signal may be changed by the control signal from the external control device 3200.

Furthermore, the external control device 3200 applies various types of image processing to the image signal transmitted from the capsule endoscope 3100 and generates the image data for displaying the taken in-vivo image on the display device. Examples of the image processing may include, for example, various types of known signal processing such as development processing (demosaic processing), high image quality processing (such as band enhancement processing, super-resolution processing, noise reduction (NR) processing and/or camera shake correction processing) and/or scaling processing (electronic zoom processing). The external control device 3200 controls drive of the display device (not illustrated) to display the in-vivo image taken on the basis of the generated image data. Alternatively, the external control device 3200 may allow a recording device (not illustrated) to record the generated image data or allow a printing device (not illustrated) to print out the same.

Figure 16:
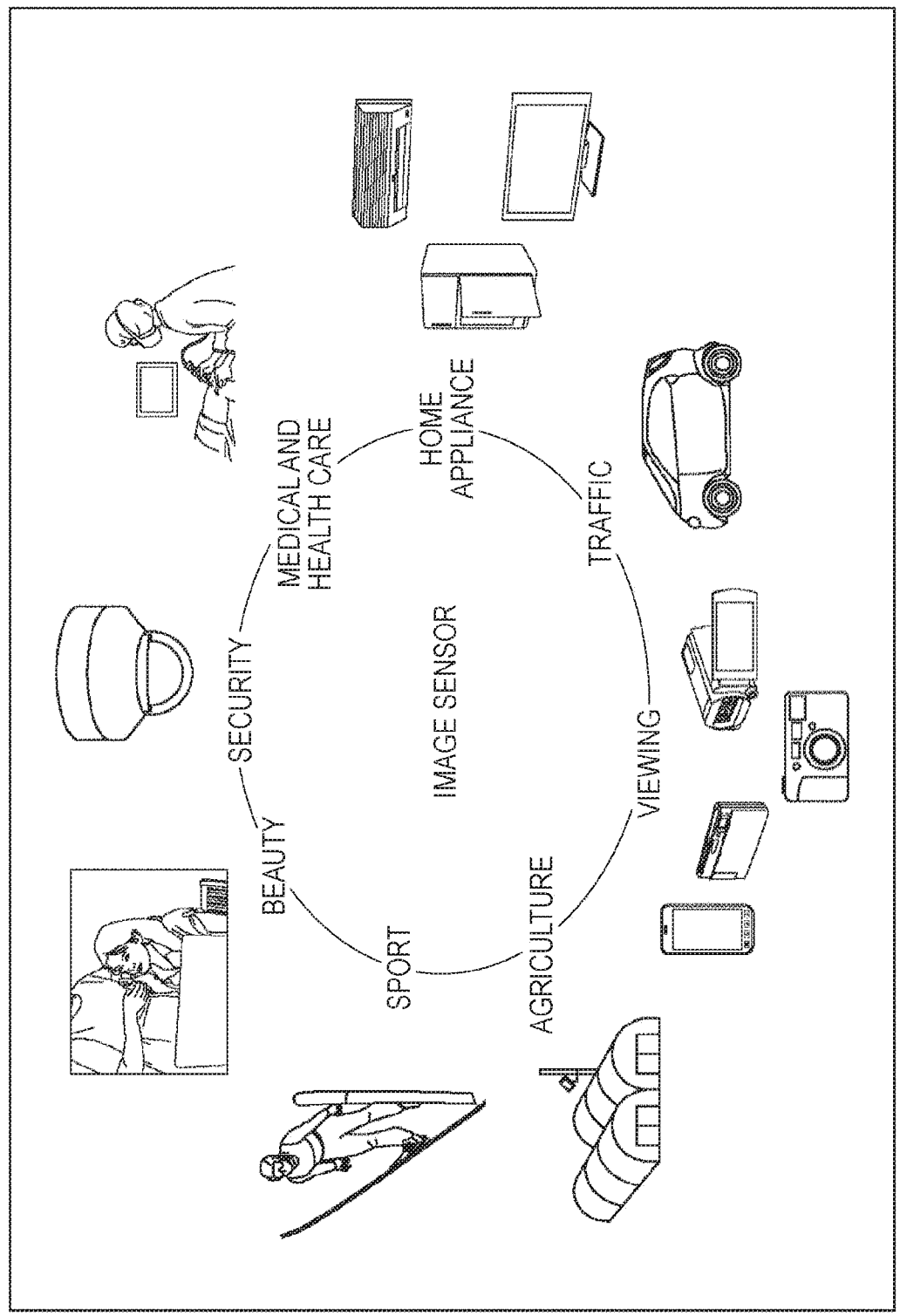
FIG. 16 is a view illustrating another application example of the first to eighth embodiments.

FIG. 16 is a view illustrating another application example of the CSP being the first to eighth embodiments.

The CSP being the first to eighth embodiments described above may be used in various cases of sensing light such as visible light, infrared light, ultraviolet light, and X-ray as follows, for example.

A device which takes an image to be used for viewing such as a digital camera and a portable device with a camera function.

A device for traffic purpose such as an in-vehicle sensor which takes images of the front, rear, surroundings, interior and the like of an automobile, a surveillance camera for monitoring traveling vehicles and roads, and a ranging sensor which measures a distance between vehicles and the like for safe driving such as automatic stop recognition of a driver's condition, and the like.

A device for home appliance such as a television, a refrigerator, and an air conditioner which takes an image of a user gesture and performs device operation according to the gesture.

A device for medical and health care use such as an endoscope and a device which performs angiography by receiving infrared light.

A device for security use such as a security monitoring camera and an individual certification camera.

A device for beauty care such as a skin condition measuring device which takes an image of skin and a microscope which takes an image of scalp.

A device for sporting use such as an action camera and a wearable camera for sporting use and the like.

A device for agricultural use such as a camera for monitoring land and crop states.

Application Example to Endoscopic Surgery System

The technology according to the present disclosure (present technology) may be applied to various products. The technology according to the present disclosure may also be applied to an endoscopic surgery system, for example.

Figure 17:
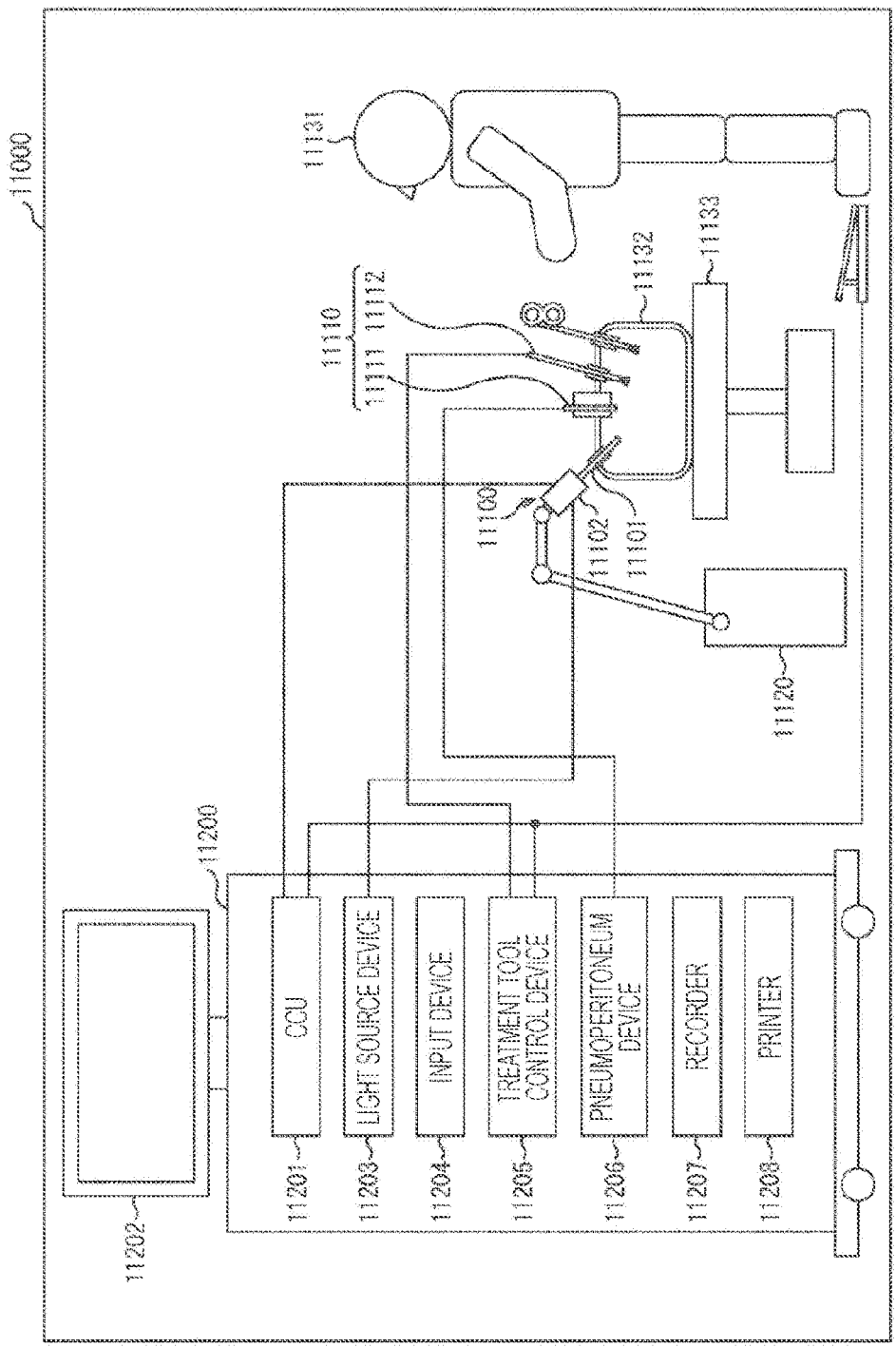
FIG. 17 is a view illustrating an example of a schematic configuration of an endoscopic surgery system.

FIG. 17 is a view illustrating an example of a schematic configuration of an endoscopic surgery system to which the technology according to the present disclosure (present technology) may be applied, for example.

FIG. 17 illustrates a state in which an operator (doctor) 11131 performs surgery on a patient 11132 on a patient bed 11133 using an endoscopic surgery system 11000. As illustrated, the endoscopic surgery system 11000 includes an endoscope 11100, other surgical tools 11110 such as a pneumoperitoneum tube 11111 and an energy treatment tool 11112, a support arm device 11120 which supports the endoscope 11100, and a cart 11200 on which various devices for endoscopic surgery are mounted.

The endoscope 11100 includes a lens tube 11101 a region of a predetermined length from a distal end of which is inserted into a body cavity of the patient 11132 and a camera head 11102 connected to a proximal end of the lens tube 11101. In the illustrated example, the endoscope 11100 configured as a so-called rigid scope having a rigid lens tube 11101 is illustrated, but the endoscope 11100 may also be configured as a so-called flexible scope having a flexible lens tube.

At the distal end of the lens tube 11101, an opening into which an objective lens is fitted is provided. A light source device 11203 is connected to the endoscope 11100 and light generated by the light source device 11203 is guided to the distal end of the lens tube by a light guide extending inside the lens tube 11101, and applied to an observation target in the body cavity of the patient 11132 via the objective lens. Note that the endoscope 11100 may be a direct view scope, a perspective scope or a side view scope.

An optical system and an imaging element are provided inside the camera head 11102, and reflected light (observation light) from the observation target is condensed on the imaging element by the optical system. The observation light is photoelectrically converted by the imaging element, and the electric signal corresponding to the observation light, that is, the image signal corresponding to the observation image is generated. The image signal is transmitted as RAW data to a camera control unit (CCU) 11201.

The CCU 11201 is configured by a central processing unit (CPU), a graphics processing unit (GPU) and the like, and comprehensively controls operation of the endoscope 11100 and the display device 11202. Moreover, the CCU 11201 receives the image signal from the camera head 11102 and applies various types of image processing for displaying the image based on the image signal, for example, development processing (demosaic processing) and the like on the image signal.

The display device 11202 displays an image based on the image signal subjected to the image processing by the CCU 11201 under the control of the CCU 11201.

The light source device 11203 includes a light source such as, for example, a light emitting diode (LED), and supplies the endoscope 11100 with the irradiation light for taking an image of a surgical site or the like.

An input device 11204 is an input interface to the endoscopic surgery system 11000. The user may input various types of information and instructions to the endoscopic surgery system 11000 via the input device 11204. For example, the user inputs an instruction and the like to change the imaging condition (type of irradiation light, magnification, focal length and the like) by the endoscope 11100.

A treatment tool control device 11205 controls drive of the energy treatment tool 11112 for tissue cauterization, incision, blood vessel sealing or the like. A pneumoperitoneum device 11206 injects gas into the body cavity via the pneumoperitoneum tube 11111 to inflate the body cavity of the patient 11132 for the purpose of securing a visual field by the endoscope 11100 and securing a working space of the operator. A recorder 11207 is a device capable of recording various types of information regarding surgery. A printer 11208 is a device capable of printing various types of information regarding surgery in various formats such as text, image, or graph.

Note that the light source device 11203 for supplying the irradiation light for taking an image of the surgical site to the endoscope 11100 may include, for example, an LED, a laser light source, or a white light source obtained by combining them. Since output intensity and output timing of each color (each wavelength) may be controlled with a high degree of accuracy in a case where the white light source is configured by the combination of RGB laser light sources, the light source device 11203 may adjust white balance of the taken image. Furthermore, in this case, by irradiating the observation target with the laser light from each of the RGB laser light sources in time division manner and controlling the drive of the imaging element of the camera head 11102 in synchronism with the irradiation timing, it is possible to take images corresponding to RGB in time division manner. According to this method, a color image may be obtained without providing a color filter in the imaging element.

Furthermore, the drive of the light source device 11203 may be controlled such that the intensity of light to be output is changed at a predetermined time interval. By controlling the drive of the imaging element of the camera head 11102 in synchronization with the timing of the change of the light intensity to obtain images in a time division manner and combining the images, an image of a high dynamic range without black defect and halation may be generated.

Furthermore, the light source device 11203 may be configured to be able to supply light of a predetermined wavelength band corresponding to special light observation. In the special light observation, for example, by using wavelength dependency of absorption of light in the body tissue, by applying light of a narrower band than that of the irradiation light (in other words, white light) at ordinary observation, so-called narrow band imaging is performed in which predetermined tissue such as the blood vessel in the mucosal surface layer is photographed with high contrast. Alternatively, in the special light observation, fluorescent observation for obtaining an image by fluorescence generated by irradiation of the excitation light may be performed. In the fluorescent observation, it is possible to irradiate the body tissue with excitation light to observe the fluorescence from the body tissue (autonomous fluorescent observation) or to locally inject a reagent such as indocyanine green (ICG) to the body tissue and irradiate the body tissue with the excitation light corresponding to a fluorescent wavelength of the reagent, thereby obtaining a fluorescent image, for example. The light source device 11203 may be configured to be able to supply the narrow band light and/or excitation light corresponding to such special light observation.

Figure 18:
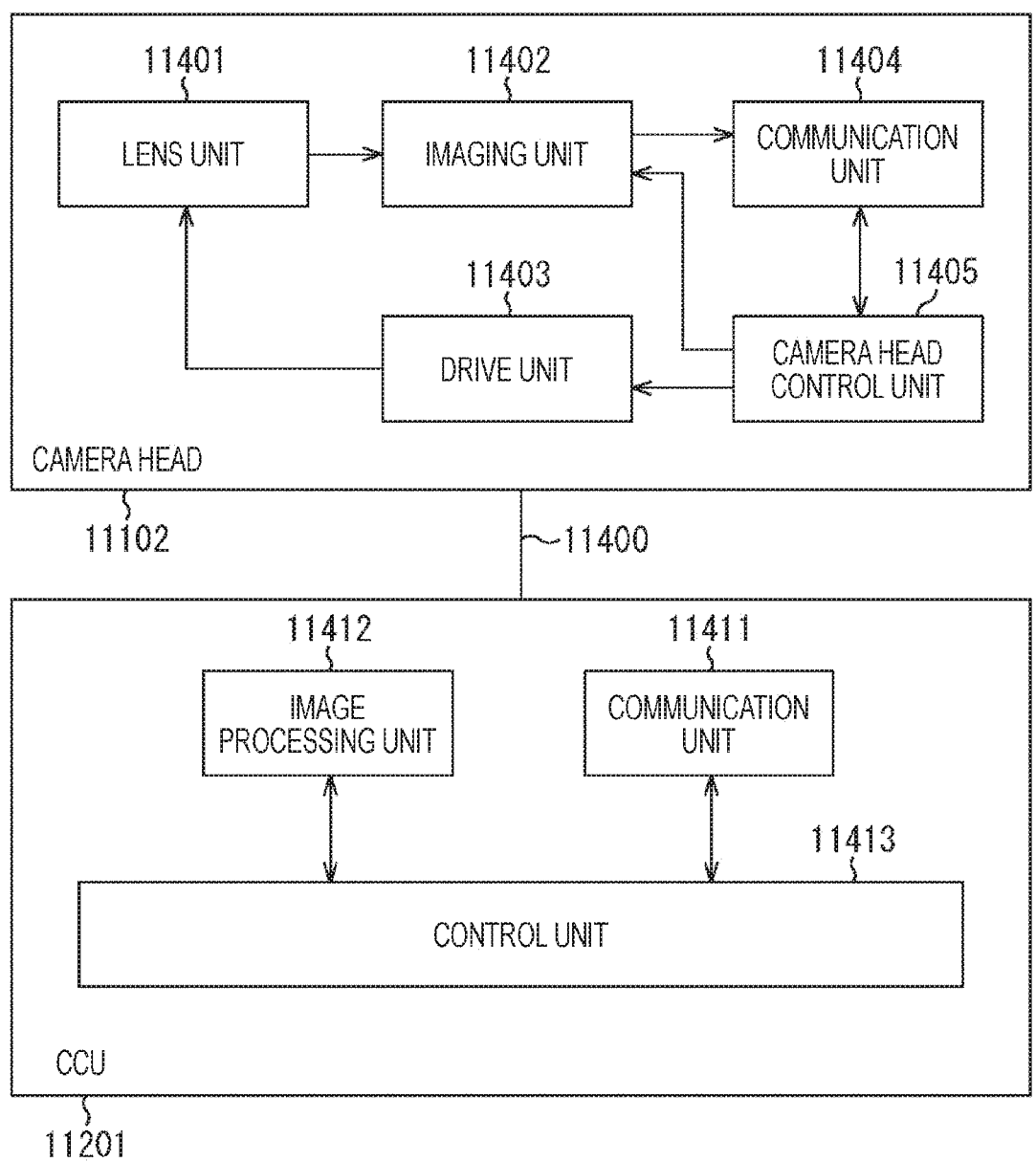
FIG. 18 is a block diagram illustrating an example of a functional configuration of a camera head and a CCU.

FIG. 18 is a block diagram illustrating an example of functional configurations of the camera head 11102 and the CCU 11201 illustrated in FIG. 17.

The camera head 11102 includes a lens unit 11401, an imaging unit 11402, a drive unit 11403, a communication unit 11404, and a camera head control unit 11405. The CCU 11201 includes a communication unit 11411, an image processing unit 11412, and a control unit 11413. The camera head 11102 and the CCU 11201 are connected to each other so as to be able to communicate by a transmission cable 11400.

The lens unit 11401 is an optical system provided at a connection to the lens tube 11101. The observation light taken in from the distal end of the lens tube 11101 is guided to the camera head 11102 and is incident on the lens unit 11401. The lens unit 11401 is obtained by combining a plurality of lenses including a zoom lens and a focus lens.

The imaging unit 11402 includes an imaging element. The imaging element forming the imaging unit 11402 may be one (a so-called single plate type) or a plurality of (so-called multiple plate type) imaging elements. In a case where the imaging unit 11402 is the multiple plate type, for example, image signals corresponding to RGB may be generated by respective imaging elements, and a color image may be obtained by combining them. Alternatively, the imaging unit 11402 may include a pair of imaging elements for obtaining right-eye and left-eye image signals corresponding to three-dimensional (3D) display. By the 3D display, the operator 11131 may grasp a depth of the living tissue in the surgical site more accurately. Note that in a case where the imaging unit 11402 is the multiple plate type, a plurality of systems of lens units 11401 may be provided corresponding to the respective imaging elements.

Furthermore, the imaging unit 11402 is not necessarily provided in the camera head 11102. For example, the imaging unit 11402 may be provided inside the lens tube 11101 immediately behind the objective lens.

The drive unit 11403 includes an actuator and moves the zoom lens and the focus lens of the lens unit 11401 by a predetermined distance along an optical axis under the control of the camera head control unit 11405. As a result, magnification and focus of the image taken by the imaging unit 11402 may be appropriately adjusted.

The communication unit 11404 includes a communication device for transmitting and receiving various types of information to and from the CCU 11201. The communication unit 11404 transmits the image signal obtained from the imaging unit 11402 as the RAW data to the CCU 11201 via the transmission cable 11400.

Furthermore, the communication unit 11404 receives the control signal for controlling the drive of the camera head 11102 from the CCU 11201 and supplies the same to the camera head control unit 11405. The control signal includes, for example, information regarding imaging conditions such as information specifying the frame rate of the taken image, information specifying the exposure value at the time of imaging, and/or information specifying magnification and focal point of the taken image.

Note that the imaging conditions such as the above-described frame rate, exposure value, magnification, and focal point may be appropriately specified by the user or automatically set by the control unit 11413 of the CCU 11201 on the basis of the obtained image signal. In the latter case, a so-called auto exposure (AE) function, an auto focus (AF) function, and an auto white balance (AWB) function are included in the endoscope 11100.

The camera head control unit 11405 controls the drive of the camera head 11102 on the basis of the control signal from the CCU 11201 received via the communication unit 11404.

The communication unit 11411 includes a communication device for transmitting and receiving various types of information to and from the camera head 11102. The communication unit 11411 receives the image signal transmitted from the camera head 11102 via the transmission cable 11400.

Furthermore, the communication unit 11411 transmits a control signal for controlling the drive of the camera head 11102 to the camera head 11102. The image signal and the control signal may be transmitted by electric communication, optical communication and the like.

The image processing unit 11412 performs various types of image processing on the image signal which is the RAW data transmitted from the camera head 11102.

The control unit 11413 performs various types of control regarding imaging of the surgical site or the like by the endoscope 11100 and display of the taken images obtained by imaging of the surgical site or the like. For example, the control unit 11413 generates a control signal for controlling the drive of the camera head 11102.

Furthermore, the control unit 11413 allows the display device 11202 to display the taken image of the surgical site or the like on the basis of the image signal subjected to the image processing by the image processing unit 11412. In this case, the control unit 11413 may recognize various objects in the taken image using various image recognition technologies. For example, the control unit 11413 may detect a shape, color and the like of an edge of the object included in the taken image, thereby recognizing the surgical tool such as forceps, the specific living-body site, the bleeding, mist when using the energy treatment tool 11112 and the like. When allowing the display device 11202 to display the taken image, the control unit 11413 may superimpose to display various types of surgery support information on the image of the surgical site using a recognition result. The surgery support information is superimposed to be displayed, and presented to the operator 11131, so that it becomes possible to reduce the burden on the operator 11131 and enabling the operator 11131 to reliably proceed with surgery.

The transmission cable 11400 connecting the camera head 11102 and the CCU 11201 is an electric signal cable corresponding to communication of electric signals, an optical fiber compatible with optical communication, or a composite cable thereof.

Here, in the illustrated example, communication is performed by wire using the transmission cable 11400, but communication between the camera head 11102 and the CCU 11201 may be performed wirelessly.

An example of the endoscopic surgery system to which the technology according to the present disclosure may be applied is described above. Note that, although the endoscopic surgery system is herein described as an example, the technology according to the present disclosure may also be applied to other examples, for example, a microscopic surgery system and the like.

Application Example to Mobile Body

The technology according to the present disclosure (present technology) may be applied to various products. For example, the technology according to the present disclosure may be realized as a device mounted on any type of mobile body such as an automobile, an electric vehicle, a hybrid electric vehicle, a motorcycle, a bicycle, a personal mobility, an airplane, a drone, a ship, and a robot.

Figure 19:
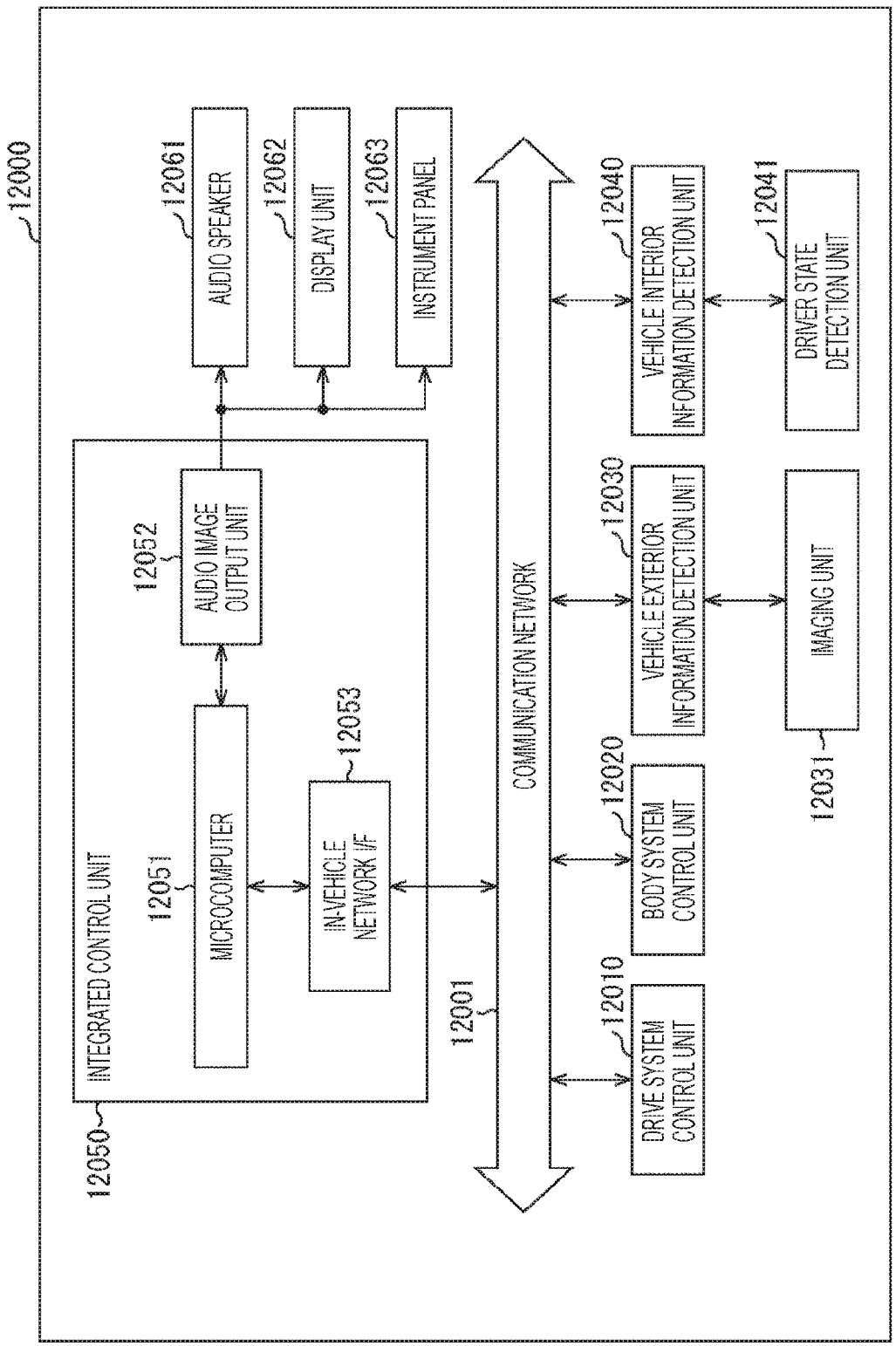
FIG. 19 is a block diagram illustrating an example of a schematic configuration of a vehicle control system.

FIG. 19 is a block diagram illustrating a schematic configuration example of a vehicle control system which is an example of a mobile body control system to which the technology according to the present disclosure may be applied.

A vehicle control system 12000 is provided with a plurality of electronic control units connected to one another via a communication network 12001. In the example illustrated in FIG. 19, the vehicle control system 12000 includes a drive system control unit 12010, a body system control unit 12020, a vehicle exterior information detection unit 12030, a vehicle interior information detection unit 12040, and an integrated control unit 12050. Furthermore, a microcomputer 12051, an audio image output unit 12052, and an in-vehicle network interface (I/F) 12053 are illustrated as functional configurations of the integrated control unit 12050.

The drive system control unit 12010 controls operation of the device regarding a drive system of the vehicle according to the various programs. For example, the drive system control unit 12010 serves as a control device of a driving force generating device for generating driving force of a vehicle such as an internal combustion engine and a driving motor, a driving force transmitting mechanism for transmitting driving force to wheels, a steering mechanism for adjusting a rudder angle of the vehicle, a braking device for generating braking force of the vehicle and the like.

The body system control unit 12020 controls operation of various devices mounted on the vehicle body according to various programs. For example, the body system control unit 12020 serves as a control device of a keyless entry system, a smart key system, a power window device, or various types of lights such as a head light, a backing light, a brake light, a turn signal light, or a fog light. In this case, a radio wave transmitted from a portable device that substitutes for a key or signals of various switches may be input to the body system control unit 12020. The body system control unit 12020 receives input of the radio wave or signals and controls a door lock device, the power window device, the lights and the like of the vehicle.

The vehicle exterior information detection unit 12030 detects information outside the vehicle on which the vehicle control system 12000 is mounted. For example, the imaging unit 12031 is connected to the vehicle exterior information detection unit 12030. The vehicle exterior information detection unit 12030 allows the imaging unit 12031 to take an image of the exterior of the vehicle and receives the taken image. The vehicle exterior information detection unit 12030 may perform detection processing of objects such as a person, a vehicle, an obstacle, a sign, and a character on a road surface or distance detection processing on the basis of the received image.

The imaging unit 12031 is an optical sensor that receives light and outputs an electric signal corresponding to an amount of received light. The imaging unit 12031 may output the electric signal as the image or output the same as ranging information. Furthermore, the light received by the imaging unit 12031 may be visible light or invisible light such as infrared light.

The vehicle interior information detection unit 12040 detects information in the vehicle. The vehicle interior information detection unit 12040 is connected to, for example, a driver state detection unit 12041 for detecting the state of the driver. The driver state detection unit 12041 includes, for example, a camera that images the driver, and the vehicle interior information detection unit 12040 may calculate a driver's fatigue level or concentration level on the basis of the detection information input from the driver state detection unit 12041 or may determine whether the driver is not dozing.

The microcomputer 12051 calculates a control target value of the driving force generating device, the steering mechanism or the braking device on the basis of the information inside and outside the vehicle obtained by the vehicle exterior information detection unit 12030 or the vehicle interior information detection unit 12040, and output a control instruction to the drive system control unit 12010. For example, the microcomputer 12051 may perform cooperative control for realizing functions of advanced driver assistance system (ADAS) including collision avoidance or impact attenuation of the vehicle, follow-up travel based on the distance between the vehicles, vehicle speed maintaining travel, vehicle collision warning, vehicle lane departure warning or the like.

Furthermore, the microcomputer 12051 may perform the cooperative control for realizing automatic driving and the like to autonomously travel independent from the operation of the driver by controlling the driving force generating device, the steering mechanism, the braking device or the like on the basis of the information of the surroundings of the vehicle obtained by the vehicle exterior information detection unit 12030 or the vehicle interior information detection unit 12040.

Furthermore, the microcomputer 12051 may output the control instruction to the body system control unit 12020 on the basis of the information outside the vehicle obtained by the vehicle exterior information detection unit 12030. For example, the microcomputer 12051 may perform the cooperative control to realize glare protection such as controlling the head light according to a position of a preceding vehicle or an oncoming vehicle detected by the vehicle exterior information detection unit 12030 to switch a high beam to a low beam.

The audio image output unit 12052 transmits at least one of audio or image output signals to an output device capable of visually or audibly notifying an occupant of the vehicle or the outside the vehicle of the information. In the example of FIG. 19, as the output device, an audio speaker 12061, a display unit 12062, and an instrument panel 12063 are illustrated. The display unit 12062 may include at least one of an on-board display or a head-up display, for example.

Figure 20:
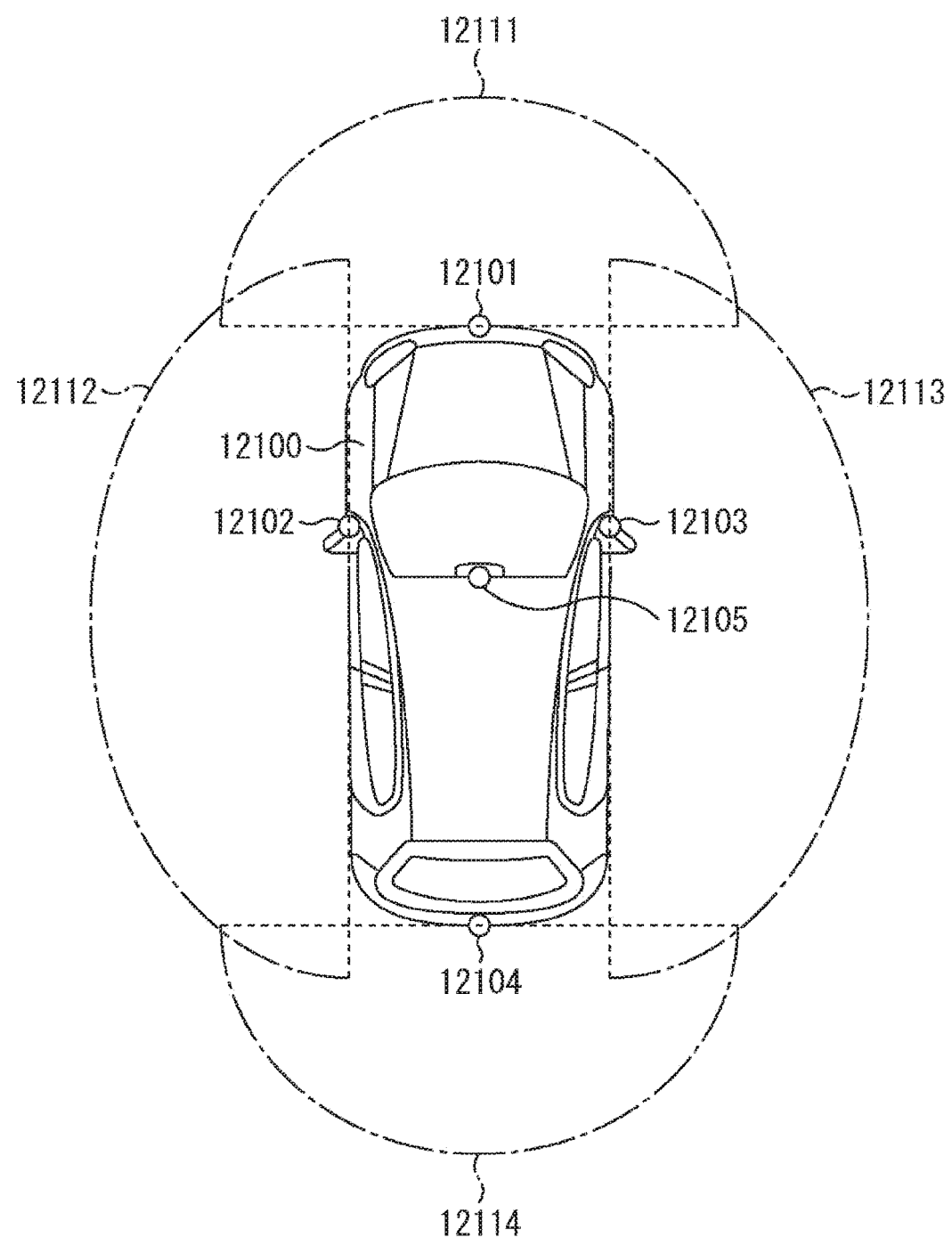
FIG. 20 is an illustrative diagram illustrating an example of an installation position of a vehicle exterior information detection unit and an imaging unit.

FIG. 20 is a view illustrating an example of an installation position of the imaging unit 12031.

In FIG. 20, a vehicle 12100 includes imaging units 12101, 12102, 12103, 12104, and 12105 as the imaging unit 12031.

The imaging units 12101, 12102, 12103, 12104, and 12105 are provided in positions such as, for example, a front nose, a side mirror, a rear bumper, a rear door, and an upper portion of a front window in a vehicle interior of the vehicle 12100. The imaging unit 12101 provided on the front nose and the imaging unit 12105 provided in the upper portion of the front window in the vehicle interior principally obtain images in front of the vehicle 12100. The imaging units 12102 and 12103 provided on the side mirrors principally obtain images of the sides of the vehicle 12100. The imaging unit 12104 provided on the rear bumper or the rear door principally obtains an image behind the vehicle 12100. The images in front obtained by the imaging units 12101 and 12105 are principally used for detecting the preceding vehicle, a pedestrian, an obstacle, a traffic signal, a traffic sign, a lane or the like.

Note that FIG. 20 illustrates an example of imaging ranges of the imaging units 12101 to 12104. The imaging range 12111 indicates the imaging range of the imaging unit 12101 provided on the front nose, the imaging ranges 12112 and 12113 indicate the imaging ranges of the imaging units 12102 and 12103 provided on the side mirrors, and the imaging range 12114 indicates the imaging range of the imaging unit 12104 provided on the rear bumper or the rear door. For example, image data taken by the imaging units 12101 to 12104 are superimposed, so that an overhead view image of the vehicle 12100 as seen from above is obtained.

At least one of the imaging units 12101 to 12104 may have a function of obtaining distance information. For example, at least one of the imaging units 12101 to 12104 may be a stereo camera including a plurality of imaging elements, or may be an imaging element having pixels for phase difference detection.

For example, the microcomputer 12051 may extract especially a closest three-dimensional object on a traveling path of the vehicle 12100, the three-dimensional object traveling at a predetermined speed (for example, 0 km/h or higher) in a direction substantially the same as that of the vehicle 12100 as the preceding vehicle by obtaining a distance to each three-dimensional object in the imaging ranges 12111 to 12114 and change in time of the distance (relative speed relative to the vehicle 12100) on the basis of the distance information obtained from the imaging units 12101 to 12104. Moreover, the microcomputer 12051 may set an inter-vehicle distance to be secured in advance from the preceding vehicle, and may perform automatic brake control (including follow-up stop control), automatic acceleration control (including follow-up start control) and the like. In this manner, it is possible to perform the cooperative control for realizing automatic driving or the like to autonomously travel independent from the operation of the driver.

For example, the microcomputer 12051 may extract three-dimensional object data regarding the three-dimensional object while sorting the same into a two-wheeled vehicle, a regular vehicle, a large vehicle, a pedestrian, and other three-dimensional object such as a utility on the basis of the distance information obtained from the imaging units 12101 to 12104 and use for automatically avoiding obstacles. For example, the microcomputer 12051 discriminates obstacles around the vehicle 12100 into an obstacle visible to a driver of the vehicle 12100 and an obstacle difficult to see. Then, the microcomputer 12051 determines a collision risk indicating a degree of risk of collision with each obstacle, and when the collision risk is higher than a set value and there is a possibility of collision, this may perform driving assistance for avoiding the collision by outputting an alarm to the driver via the audio speaker 12061 and the display unit 12062 or performing forced deceleration or avoidance steering via the drive system control unit 12010.

At least one of the imaging units 12101 to 12104 may be an infrared camera for detecting infrared rays. For example, the microcomputer 12051 may recognize a pedestrian by determining whether there is a pedestrian in the taken images of the imaging units 12101 to 12104. Such pedestrian recognition is carried out, for example, by a procedure of extracting feature points in the taken images of the imaging units 12101 to 12104 as infrared cameras and a procedure of performing pattern matching processing on a series of feature points indicating an outline of an object to discriminate whether this is a pedestrian. When the microcomputer 12051 determines that there is a pedestrian in the taken images of the imaging units 12101 to 12104 and recognizes the pedestrian, the audio image output unit 12052 controls the display unit 12062 to superimpose a rectangular contour for emphasis on the recognized pedestrian. Furthermore, the audio image output unit 12052 may control the display unit 12062 to display icons or the like indicating pedestrians at desired positions.

An example of the vehicle control system to which the technology according to the present disclosure is applicable is heretofore described.

Note that embodiments of the present disclosure are not limited to the above-described embodiments, and various modifications may be made without departing from the gist of the present disclosure.

The present disclosure may also take the following configuration.

(1)

A chip size package provided with:

a solid-state imaging element that generates a pixel signal according to incident light; and a light emitting element that outputs irradiation light according to voltage applied, in which the solid-state imaging element and the light emitting element are integrated.

(2)

The chip size package according to (1) described above, in which the solid-state imaging element is obtained by stacking a first layer in which a pixel array that performs photoelectric conversion is formed, and a second layer in which at least a signal processing circuit for processing the pixel signal converted by the pixel array and an I/O circuit are formed, and the signal processing circuit and the I/O circuit formed in the second layer are arranged so as not to protrude in a lateral direction from a region occupied by the pixel array.

(3)

The chip size package according to (1) or (2) described above, in which the light emitting element is formed using sapphire glass as a support substrate.

(4)

The chip size package according to (2) described above, in which the sapphire glass also serves as a cover glass of the solid-state imaging element.

(5)

The chip size package according to any one of (1) to (4) described above, in which a first substrate on which a plurality of light emitting elements is formed and a second substrate on which a plurality of solid-state imaging elements is formed are bonded to each other by a WCSP manufacturing method and then singulated.

(6)

The chip size package according to any one of (1) to (4) described above, in which a plurality of solid-state imaging elements is mounted on a substrate on which a plurality of light emitting elements is formed by a COW manufacturing method and then singulated.

(7)

The chip size package according to (6) described above, in which the solid-state imaging element mounted on the substrate on which the plurality of light emitting elements is formed by the COW manufacturing method is made a CSP, and a solder ball is formed as a connection terminal on the CSP solid-state imaging element.

(8)

The chip size package according to (6) described above in which a wire is connected as a connection terminal to the solid-state imaging element mounted on the substrate on which the plurality of light emitting elements is formed by the COW manufacturing method.

(9)

The chip size package according to any one of (1) to (4) described above, in which a plurality of light emitting elements is mounted on a substrate on which a plurality of solid-state imaging elements is formed by a COW manufacturing method and then singulated.

(10)

The chip size package according to any one of (1) to (9) described above, in which the light emitting element is an LED element or a laser element.

(11)

The chip size package according to any one of (1) to (10) described above, in which a moth-eye processed portion for adjusting directivity of the irradiation light output from the light emitting element is formed on the sapphire glass.

(12)

The chip size package according to any one of (1) to (11) described above, in which a light shielding wall is formed at a boundary between the light emitting element and the solid-state imaging element.

(13)

The chip size package according to any one of (1) to (12) described above, in which a light shielding groove is formed in the sapphire glass located at the boundary between the light emitting element and the solid-state imaging element.

(14)

A method of manufacturing a chip size package provided with:

a solid-state imaging element that generates a pixel signal according to incident light; and a light emitting element that outputs irradiation light according to voltage applied, the solid-state imaging element and the light emitting element being integrated, the method provided with:

applying sealing resin to a second substrate on which a plurality of solid-state imaging elements is formed;

bonding a first substrate on which a plurality of light emitting elements is formed to the second substrate to which the sealing resin is applied by a WCSP manufacturing method; and singulating the bonded first and second substrates.

(15)

An electronic device provided with:

a chip size package obtained by integrating a solid-state imaging element that generates a pixel signal according to incident light, and a light emitting element that outputs irradiation light according to voltage applied.

(16)

An endoscope provided with:

a chip size package obtained by integrating a solid-state imaging element that generates a pixel signal according to incident light, and a light emitting element that outputs irradiation light according to voltage applied.

REFERENCE SIGNS LIST

10 Solid-state imaging element
11 Cover glass
12 On-chip lens
13 Color filter
14 PD layer
15 Wiring layer
16, 25, 26, 44, 46, 47, 61, 62 Solder ball
20 Blue LED element
21 Sapphire glass
22 n layer
23 Light emitting layer
24 p layer
25$n$, 25$p$ Wire bonding pad
30, 50, 70, 90, 120, 130, 140, 150 CSP
41 Protective film
42 Sealing resin
43, 45 VIA
81, 82, 83 Wire
120 CSP
121 Moth-eye processed portion
130 CSP
131 Light shielding wall
140 CSP
141 Light shielding groove
150 CSP
3000 In-vivo information obtaining system
3100 Capsule endoscope
3101 Capsule-shaped casing 3103 Light source unit
3105 Imaging unit
3107 Image processing unit
3109 Wireless communication unit
3111, 3201 Antenna
3115 Power supply unit
3117 State detection unit
3119 Control unit
3200 External control device
11000 Endoscopic surgery system
11100 Endoscope
11101 Lens tube
11102 Camera head
11110 Other surgical tools
11111 Pneumoperitoneum tube
11112 Energy treatment tool
11120 Support arm device
11131 Operator (doctor)
11132 Patient
11133 Patient bed
11200 Cart
11201 Camera control unit (CCU)
11202 Display device
11203 Light source device
11204 Input device
11205 Treatment tool control device
11206 Pneumoperitoneum device
11207 Recorder
11208 Printer

The invention claimed is:

1. A chip size package, comprising:
a solid-state imaging element configured to generate a pixel signal based on incident light; and
a light emitting element configured to output irradiation light based on voltage applied, wherein
the solid-state imaging element is integrated with the light emitting element,
the light emitting element includes sapphire glass as a support substrate,
the sapphire glass includes a light shielding groove,
the light shielding groove extends from a top surface of the sapphire glass to a bottom surface of the sapphire glass, and
the light shielding groove in the sapphire glass is at a boundary between the light emitting element and the solid-state imaging element.

2. The chip size package according to claim 1, wherein the sapphire glass further serves as a cover glass of the solid-state imaging element.

3. The chip size package according to claim 1, wherein
the solid-state imaging element comprises a stack of a first layer and a second layer,
the first layer comprises a pixel array configured to execute photoelectric conversion,
the second layer comprises a signal processing circuit and an I/O circuit,
the signal processing circuit is configured to process the pixel signal converted by the pixel array, and
the signal processing circuit and the I/O circuit in the second layer are arranged so as not to protrude in a lateral direction from a region occupied by the pixel array.

4. The chip size package according to claim 3, further comprising a first substrate on which the light emitting element is formed, and a second substrate on which the solid-state imaging element is formed, wherein
the first substrate is bonded to the second substrate by a wafer level chip size package (WCSP) manufacturing method, and
the first substrate and the second substrate are singulated by a singlulation process.

5. The chip size package according to claim 3, wherein
the solid-state imaging element is mounted on a substrate on which the light emitting element is formed, the solid-state imaging element is mounted by a chip on wafer (COW) manufacturing method, and the substrate is singulated by a singlulation process.

6. The chip size package according to claim 5, wherein
the solid-state imaging element mounted on the substrate by the COW manufacturing method is a chip size package (CSP) solid-state imaging element, and
the CSP solid-state imaging element comprises a solder ball as a connection terminal.

7. The chip size package according to claim 5, further comprising a wire connected as a connection terminal to the solid-state imaging element mounted on the substrate on which the light emitting element is formed by the COW manufacturing method.

8. The chip size package according to claim 3, wherein the light emitting element is mounted on a substrate on which the solid-state imaging element is formed by a chip on wafer (COW) manufacturing method, and the substrate is singulated by a singlulation process.

9. The chip size package according to claim 3, wherein the light emitting element is one of an LED element or a laser element.

10. The chip size package according to claim 3, wherein the sapphire glass comprises a moth-eye processed portion configured to adjust directivity of the irradiation light output from the light emitting element.

11. The chip size package according to claim 3, further comprising a light shielding wall at the boundary between the light emitting element and the solid-state imaging element.

12. A method of manufacturing a chip size package, the method comprising:
applying sealing resin to a second substrate on which a plurality of solid-state imaging elements is formed;
bonding a first substrate on which a plurality of light emitting elements is formed to the second substrate to which the sealing resin is applied, wherein the first substrate is bonded to the second substrate by a wafer level chip size package (WCSP) manufacturing method; and
singulating the bonded first substrate and the second substrate, wherein the chip size package includes:
a solid-state imaging element of the plurality of solid-state imaging elements configured to generate a pixel signal according to incident light; and
a light emitting element of the plurality of light emitting elements configured to output irradiation light according to voltage applied, wherein the solid-state imaging element is integrated with the light emitting element.

13. An electronic device, comprising:
a chip size package that includes a solid-state imaging element and a light emitting element, wherein
the solid-state imaging element is integrated with the light emitting element,
the solid-state imaging element is configured to generate pixel signal based on incident light,
the light emitting element is configured to output irradiation light based on voltage applied, the light emitting element includes sapphire glass as a support substrate,
the sapphire glass includes a light shielding groove,
the light shielding groove extends from a top surface of the sapphire glass to a bottom surface of the sapphire glass, and
the light shielding groove in the sapphire glass is at a boundary between the light emitting element and the solid-state imaging element.

14. An endoscope, comprising:
a chip size package that includes a solid-state imaging element and a light emitting element, wherein
the solid-state imaging element is integrated with the light emitting element,
the solid-state imaging element is configured to generate a pixel signal based on incident light,
the light emitting element is configured to output irradiation light based on voltage applied,
the light emitting element includes sapphire glass as a support substrate,
the sapphire glass includes a light shielding groove,
the light shielding groove extends from a top surface of the sapphire glass to a bottom surface of the sapphire glass, and
the light shielding groove in the sapphire glass is at a boundary between the light emitting element and the solid-state imaging element.

* * * * *